United States Patent
Clausen et al.

(10) Patent No.: US 12,220,330 B2
(45) Date of Patent: Feb. 11, 2025

(54) PROSTHETIC FOOT WITH ENHANCED STABILITY AND ELASTIC ENERGY RETURN

(71) Applicant: Össur Iceland ehf, Reykjavík (IS)

(72) Inventors: Arinbjorn Viggo Clausen, Reykjavik (IS); Bjarni Andresson, Seltjarnarnes (IS); Vilhjalmur Freyr Jonsson, Reykjavik (IS); Christophe Lecomte, Reykjavik (IS)

(73) Assignee: Össur Iceland ehf, Reykjavík (IS)

( * ) Notice: Subject to any disclaimer, the term of this patent is extended or adjusted under 35 U.S.C. 154(b) by 538 days.

(21) Appl. No.: 17/677,194

(22) Filed: Feb. 22, 2022

(65) Prior Publication Data
US 2022/0249260 A1 Aug. 11, 2022

Related U.S. Application Data

(63) Continuation of application No. 16/374,055, filed on Apr. 3, 2019, now Pat. No. 11,285,024, which is a
(Continued)

(51) Int. Cl.
*A61F 2/66* (2006.01)
*A61F 2/70* (2006.01)
(Continued)

(52) U.S. Cl.
CPC ............. *A61F 2/6607* (2013.01); *A61F 2/66* (2013.01); *A61F 2/70* (2013.01);
(Continued)

(58) Field of Classification Search
CPC ...... A61F 2002/5006; A61F 2002/5007; A61F 2002/503; A61F 2002/5033;
(Continued)

(56) References Cited

U.S. PATENT DOCUMENTS

| | | |
|---|---|---|
| 909,859 A | 1/1909 | Apgar |
| 2,475,373 A | 7/1949 | Catranis |

(Continued)

FOREIGN PATENT DOCUMENTS

| | | |
|---|---|---|
| CA | 2 405 356 | 10/2001 |
| CA | 2 494 365 | 3/2004 |

(Continued)

OTHER PUBLICATIONS

Abbas et al., "Neural Network Control of Functional Neuromuscular Stimulation Systems: Computer Stimulation Studies," IEEE Transactions on Biomedical Engineering, vol. 42, No. 11, Nov. 1995, pp. 1117-1127.
(Continued)

*Primary Examiner* — Christie Bahena
(74) *Attorney, Agent, or Firm* — Knobbe, Martens, Olson & Bear, LLP

(57) ABSTRACT

A prosthetic foot comprises an attachment member and two or more flexible members. The attachment member can include a connector configured to connect the attachment member to a user or another prosthetic device. The two or more flexible members can be rotatably attached to the attachment member by rotatable joints such that the flexible members can both rotate and flex relative to the attachment member when the prosthetic foot contacts the ground.

14 Claims, 19 Drawing Sheets

Related U.S. Application Data continuation of application No. 15/386,366, filed on Dec. 21, 2016, now Pat. No. 10,369,019, which is a continuation of application No. 14/188,216, filed on Feb. 24, 2014, now Pat. No. 9,561,118.

(60) Provisional application No. 61/770,212, filed on Feb. 27, 2013, provisional application No. 61/769,405, filed on Feb. 26, 2013.

(51) Int. Cl.
 *A61F 2/50* (2006.01)
 *A61F 2/74* (2006.01)
 *A61F 2/76* (2006.01)

(52) U.S. Cl.
 CPC . *A61F 2002/5006* (2013.01); *A61F 2002/503* (2013.01); *A61F 2002/5033* (2013.01); *A61F 2002/5079* (2013.01); *A61F 2002/6657* (2013.01); *A61F 2002/6664* (2013.01); *A61F 2002/6671* (2013.01); *A61F 2002/701* (2013.01); *A61F 2/74* (2021.08); *A61F 2002/7615* (2013.01)

(58) Field of Classification Search
 CPC ...... A61F 2002/5079; A61F 2002/6614; A61F 2002/6642; A61F 2002/6657; A61F 2002/6664; A61F 2002/665; A61F 2002/6671; A61F 2002/6692; A61F 2002/701; A61F 2002/74; A61F 2002/7615; A61F 2/66; A61F 2/6607; A61F 2/76; A61B 5/04001
 See application file for complete search history.

(56) References Cited

U.S. PATENT DOCUMENTS

| | | |
|---|---|---|
| 2,568,051 A | 9/1951 | Catranis |
| 2,619,652 A | 12/1952 | Vesper |
| 2,843,853 A | 7/1958 | Mauch |
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,557,387 A | 1/1971 | Ohlenbusch et al. |
| 3,589,134 A | 6/1971 | Hackmann |
| 3,659,294 A | 5/1972 | Glabiszewski |
| 3,701,368 A | 10/1972 | Stern |
| 3,791,375 A | 2/1974 | Pfeifer |
| 3,820,168 A | 6/1974 | Horvath |
| 3,866,246 A | 2/1975 | Seamone et al. |
| 3,871,032 A | 3/1975 | Karas |
| 3,953,900 A | 5/1976 | Thompson |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,172,433 A | 10/1979 | Bianchi et al. |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,370,977 A | 2/1983 | Mauldin et al. |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,488,320 A | 12/1984 | Wilson |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,579,558 A | 4/1986 | Ramer |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,652,266 A | 3/1987 | Truesdell |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Young et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,012,591 A | 5/1991 | Asakawa |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,101,472 A | 3/1992 | Repperger |
| 5,112,296 A | 5/1992 | Beard et al. |
| 5,112,356 A | 5/1992 | Harris et al. |
| 5,116,384 A | 5/1992 | Wilson et al. |
| 5,139,525 A | 8/1992 | Kristinsson |
| 5,153,496 A | 10/1992 | LaForge |
| 5,156,630 A | 10/1992 | Rappoport et al. |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe et al. |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnaes |
| 5,323,650 A | 6/1994 | Fullen et al. |
| 5,327,790 A | 7/1994 | Levin et al. |
| 5,336,269 A | 8/1994 | Smits |

(56) References Cited

U.S. PATENT DOCUMENTS

| | | |
|---|---|---|
| 5,357,696 A | 10/1994 | Gray et al. |
| 5,376,128 A | 12/1994 | Bozeman, Jr. |
| 5,376,133 A | 12/1994 | Gramnaes |
| 5,376,137 A | 12/1994 | Shorter et al. |
| 5,376,138 A | 12/1994 | Bouchard et al. |
| 5,376,141 A | 12/1994 | Phillips |
| 5,382,373 A | 1/1995 | Carlson et al. |
| 5,383,939 A | 1/1995 | James |
| 5,394,132 A | 2/1995 | Poil |
| 5,397,287 A | 3/1995 | Lindfors |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,425,780 A | 6/1995 | Flatt et al. |
| 5,430,643 A | 7/1995 | Seraji |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,455,497 A | 10/1995 | Hirose et al. |
| 5,472,412 A | 12/1995 | Knoth |
| 5,476,441 A | 12/1995 | Durfee et al. |
| 5,484,389 A | 1/1996 | Stark et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriquez |
| 5,800,568 A | 9/1998 | Atkinson et al. |
| 5,800,570 A | 9/1998 | Collier |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,954,621 A | 9/1999 | Joutras et al. |
| 5,955,667 A | 9/1999 | Fyfe |
| 5,957,981 A | 9/1999 | Gramnaes |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,984,972 A | 11/1999 | Huston et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,029,374 A | 2/2000 | Herr et al. |
| 6,039,091 A | 3/2000 | Rodgers et al. |
| 6,061,577 A | 5/2000 | Andrieu et al. |
| 6,071,313 A | 6/2000 | Phillips |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,122,960 A | 9/2000 | Hutchings et al. |
| 6,129,690 A | 10/2000 | Hamlin et al. |
| 6,129,766 A | 10/2000 | Johnson et al. |
| 6,139,586 A | 10/2000 | Wagner et al. |
| 6,151,624 A | 11/2000 | Teare et al. |
| 6,164,967 A | 12/2000 | Sale |
| 6,165,226 A | 12/2000 | Wagner |
| 6,168,634 B1 | 1/2001 | Schmitz |
| 6,183,425 B1 | 2/2001 | Whalen et al. |
| 6,185,614 B1 | 2/2001 | Cuomo et al. |
| 6,187,051 B1 | 2/2001 | Gerad van de Veen |
| 6,187,052 B1 | 2/2001 | Molino et al. |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| 6,241,776 B1 | 6/2001 | Christensen |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,378,190 B2 | 4/2002 | Akeel |
| 6,379,393 B1 | 4/2002 | Mavroidis et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,482,236 B1 | 11/2002 | Habecker |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,828 B1 | 2/2003 | Fyfe et al. |
| 6,517,858 B1 | 2/2003 | Le Moel et al. |

(56) References Cited

U.S. PATENT DOCUMENTS

| | | |
|---|---|---|
| 6,522,266 B1 | 2/2003 | Soehren et al. |
| 6,537,322 B1 | 3/2003 | Johnson et al. |
| 6,543,987 B2 | 4/2003 | Ehrat |
| 6,562,075 B2 | 5/2003 | Townsend et al. |
| 6,574,655 B1 | 6/2003 | Libert et al. |
| 6,587,728 B2 | 7/2003 | Fang et al. |
| 6,589,287 B2 | 7/2003 | Lundborg |
| 6,599,439 B2 | 7/2003 | Iregar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,708,103 B2 | 3/2004 | Herr et al. |
| 6,719,806 B1 | 4/2004 | Zahedi et al. |
| 6,719,807 B2 | 4/2004 | Harris |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,770,045 B2 | 8/2004 | Naft et al. |
| 6,780,343 B2 | 8/2004 | Hata et al. |
| 6,805,677 B2 | 10/2004 | Simmons |
| 6,811,571 B1 | 11/2004 | Phillips |
| 6,813,582 B2 | 11/2004 | Levi et al. |
| 6,824,569 B2 | 11/2004 | Okediji |
| D499,487 S | 12/2004 | Bédard et al. |
| D501,925 S | 2/2005 | Bédard et al. |
| 6,855,170 B2 | 2/2005 | Gramnäs |
| 6,863,695 B2 | 3/2005 | Doddroe et al. |
| 6,875,241 B2 | 4/2005 | Christensen |
| 6,876,135 B2 | 4/2005 | Pelrine et al. |
| 6,908,488 B2 | 6/2005 | Paasivaara et al. |
| 6,910,331 B2 | 6/2005 | Asai et al. |
| 6,918,308 B2 | 7/2005 | Biedermann |
| 6,955,692 B2 | 10/2005 | Grundei |
| 6,966,882 B2 | 11/2005 | Horst |
| 6,966,933 B2 | 11/2005 | Christensen |
| 6,969,408 B2 | 11/2005 | Lecomte et al. |
| 6,972,043 B1 | 12/2005 | Biedermann |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,896 B1 | 6/2006 | Kiselik |
| 7,066,964 B2 | 6/2006 | Wild |
| 7,101,487 B2 | 9/2006 | Hsu et al. |
| 7,112,938 B2 | 9/2006 | Takenaka et al. |
| 7,118,601 B2 | 10/2006 | Yasui |
| 7,131,998 B2 | 11/2006 | Pasolini |
| 7,137,998 B2 | 11/2006 | Bédard et al. |
| 7,147,667 B2 | 12/2006 | Bédard et al. |
| 7,150,762 B2 | 12/2006 | Caspers |
| 7,164,967 B2 | 1/2007 | Etienne-Cummings et al. |
| 7,172,630 B2 | 2/2007 | Christensen |
| 7,182,738 B2 | 2/2007 | Bonutti et al. |
| 7,198,071 B2 | 4/2007 | Bisbee, III et al. |
| 7,209,788 B2 | 4/2007 | Nicolelis et al. |
| 7,211,115 B2 | 5/2007 | Townsend et al. |
| 7,226,485 B2 | 6/2007 | Townsend et al. |
| 7,279,009 B2 | 10/2007 | Herr et al. |
| 7,295,892 B2 | 11/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bédard et al. |
| 7,347,877 B2 | 3/2008 | Clausen et al. |
| 7,364,593 B2 | 4/2008 | Townsend et al. |
| 7,374,578 B2 | 5/2008 | Townsend et al. |
| 7,381,192 B2 | 6/2008 | Brodard et al. |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |
| 7,410,503 B2 | 8/2008 | Townsend et al. |
| 7,419,509 B2 | 9/2008 | Christensen |
| 7,429,272 B2 | 9/2008 | Townsend et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,503,900 B2 | 3/2009 | Goswami |
| 7,507,259 B2 | 3/2009 | Townsend et al. |
| 7,520,904 B2 | 4/2009 | Christensen |
| 7,531,006 B2 | 5/2009 | Clausen et al. |
| 7,544,172 B2 | 6/2009 | Santos-Munne et al. |
| 7,552,664 B2 | 6/2009 | Bulatowicz |
| 7,572,299 B2 | 8/2009 | Christensen |
| 7,575,602 B2 | 8/2009 | Amirouche et al. |
| 7,578,799 B2 | 8/2009 | Thorsteinsson et al. |
| 7,578,852 B2 | 8/2009 | Townsend et al. |
| 7,588,604 B2 | 9/2009 | Okuda |
| 7,611,543 B2 | 11/2009 | Townsend et al. |
| 7,618,464 B2 | 11/2009 | Christensen |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,686,848 B2 | 3/2010 | Christensen |
| 7,691,154 B2 | 4/2010 | Asgeirsson et al. |
| 7,708,784 B2 | 5/2010 | Townsend et al. |
| 7,736,394 B2 | 6/2010 | Bédard et al. |
| 7,763,082 B1 | 7/2010 | Curtis |
| 7,766,974 B2 | 8/2010 | Curtis |
| 7,794,505 B2 | 9/2010 | Clausen et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,824,446 B2 | 11/2010 | Christensen |
| 7,846,213 B2 | 12/2010 | Lecomte et al. |
| 7,862,620 B2 | 1/2011 | Clausen et al. |
| 7,867,284 B2 | 1/2011 | Bédard et al. |
| 7,867,285 B2 | 1/2011 | Clausen et al. |
| 7,883,546 B2 | 2/2011 | Kazerooni et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,951,101 B2 | 5/2011 | Pusch |
| 7,955,398 B2 | 6/2011 | Bédard et al. |
| 7,955,399 B2 | 6/2011 | Townsend et al. |
| 7,985,265 B2 | 7/2011 | Moser et al. |
| 7,992,849 B2 | 8/2011 | Sugar et al. |
| 8,007,544 B2 | 8/2011 | Jonsson et al. |
| 8,011,229 B2 | 9/2011 | Lieberman et al. |
| 8,034,121 B2 | 10/2011 | Christensen |
| 8,048,007 B2 | 11/2011 | Roy |
| 8,048,172 B2 | 11/2011 | Jonsson et al. |
| 8,057,550 B2 | 11/2011 | Clausen |
| 8,070,829 B2 | 12/2011 | Townsend et al. |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,109,890 B2 | 2/2012 | Kamiar et al. |
| 8,118,879 B2 | 2/2012 | Wilson |
| 8,122,772 B2 | 2/2012 | Clausen et al. |
| 8,142,370 B2 | 3/2012 | Weinberg et al. |
| 8,211,042 B2 | 7/2012 | Gilbert et al. |
| 8,231,687 B2 | 7/2012 | Bédard et al. |
| 8,236,062 B2 | 8/2012 | Townsend |
| 8,287,477 B1 | 10/2012 | Herr et al. |
| 8,317,876 B2 | 11/2012 | Mosler |
| 8,317,877 B2 | 11/2012 | Doddroe et al. |
| 8,323,354 B2 | 12/2012 | Bédard et al. |

(56) References Cited

U.S. PATENT DOCUMENTS

| | | |
|---|---|---|
| 8,366,788 B2 | 2/2013 | Moser et al. |
| 8,366,790 B2 | 2/2013 | Curtis |
| 8,376,971 B1 | 2/2013 | Herr et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,480,760 B2 | 7/2013 | Hansen et al. |
| 8,500,823 B2 | 8/2013 | Herr et al. |
| 8,500,825 B2 | 8/2013 | Christensen et al. |
| 8,512,415 B2 | 8/2013 | Herr et al. |
| 8,551,184 B1 | 10/2013 | Herr |
| 8,574,314 B2 | 11/2013 | Townsend |
| 8,601,897 B2 | 12/2013 | Lauzier et al. |
| 8,617,254 B2 | 12/2013 | Bisbee, III et al. |
| 8,652,218 B2 | 2/2014 | Goldfarb et al. |
| 8,657,886 B2 | 2/2014 | Clausen et al. |
| 8,702,811 B2 | 4/2014 | Ragnarsdottir et al. |
| 8,764,850 B2 | 7/2014 | Hanset et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,870,967 B2 | 10/2014 | Herr et al. |
| 8,888,864 B2 | 11/2014 | Iversen et al. |
| 8,915,968 B2 | 12/2014 | Langlois et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 10,195,057 B2 | 2/2019 | Clausen |
| 10,251,762 B2 | 4/2019 | Langlois |
| 10,299,943 B2 | 5/2019 | Clausen et al. |
| 10,307,271 B2 | 6/2019 | Holgate et al. |
| 10,369,019 B2 | 8/2019 | Clausen et al. |
| 10,390,974 B2 | 8/2019 | Clausen et al. |
| 10,405,996 B2 | 9/2019 | Langlois |
| 10,543,109 B2 | 1/2020 | Holgate |
| 10,575,970 B2 | 3/2020 | Holgate |
| 10,695,197 B2 | 6/2020 | Clausen |
| 10,940,027 B2 | 3/2021 | Langlois et al. |
| 11,007,072 B2 | 5/2021 | Gilbert et al. |
| 11,285,024 B2 | 3/2022 | Clausen et al. |
| 2001/0002772 A1 | 6/2001 | Kim et al. |
| 2002/0007690 A1 | 1/2002 | Song et al. |
| 2002/0079857 A1 | 6/2002 | Ishii et al. |
| 2002/0087216 A1 | 7/2002 | Atkinson et al. |
| 2002/0143408 A1 | 10/2002 | Townsend et al. |
| 2003/0005786 A1 | 1/2003 | Stuart et al. |
| 2003/0019700 A1 | 1/2003 | Wittig |
| 2003/0149600 A1 | 8/2003 | Williams |
| 2003/0163206 A1 | 8/2003 | Yasui |
| 2004/0064195 A1 | 4/2004 | Herr |
| 2004/0078299 A1 | 4/2004 | Down-Logan et al. |
| 2004/0083007 A1 | 4/2004 | Molino et al. |
| 2004/0153484 A1 | 8/2004 | Unno |
| 2004/0169112 A1 | 9/2004 | Grossart |
| 2004/0193286 A1 | 9/2004 | Grundei |
| 2005/0033451 A1 | 2/2005 | Aigner et al. |
| 2005/0038525 A1 | 2/2005 | Doddroe et al. |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0071017 A1 | 3/2005 | Lecomte et al. |
| 2005/0107889 A1 | 5/2005 | Bédard et al. |
| 2005/0113973 A1 | 5/2005 | Endo et al. |
| 2005/0137717 A1 | 6/2005 | Gramnaes |
| 2005/0166685 A1 | 8/2005 | Boiten |
| 2005/0192677 A1 | 9/2005 | Ragnarsdottir et al. |
| 2005/0203640 A1 | 9/2005 | Christensen |
| 2005/0216097 A1 | 9/2005 | Rifkin |
| 2005/0251079 A1 | 11/2005 | Carvey et al. |
| 2005/0283257 A1 | 12/2005 | Bisbee et al. |
| 2006/0025959 A1 | 2/2006 | Gomez et al. |
| 2006/0030950 A1 | 2/2006 | Townsend et al. |
| 2006/0069336 A1 | 3/2006 | Krebs et al. |
| 2006/0136072 A1 | 6/2006 | Bisbee et al. |
| 2006/0184252 A1 | 8/2006 | Oddsson et al. |
| 2006/0184280 A1 | 8/2006 | Oddsson et al. |
| 2006/0189899 A1 | 8/2006 | Flaherty et al. |
| 2006/0212131 A1 | 9/2006 | Curtis |
| 2006/0235545 A1 | 10/2006 | Habecker |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0027557 A1 | 2/2007 | Jonsson et al. |
| 2007/0043449 A1 | 2/2007 | Herr et al. |
| 2007/0050047 A1 | 3/2007 | Ragnarsdottir et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2007/0213841 A1 | 9/2007 | Townsend et al. |
| 2008/0004718 A1 | 1/2008 | Mosler |
| 2008/0046096 A1 | 2/2008 | Bédard et al. |
| 2008/0058668 A1 | 3/2008 | Seyed Momen et al. |
| 2008/0141813 A1 | 6/2008 | Ehrat |
| 2008/0262635 A1 | 10/2008 | Moser et al. |
| 2008/0306612 A1 | 12/2008 | Mosler |
| 2009/0012630 A1 | 1/2009 | Mosler et al. |
| 2009/0030530 A1 | 1/2009 | Martin |
| 2009/0082869 A1 | 3/2009 | Slemker et al. |
| 2009/0088912 A1 | 4/2009 | Rajaraman |
| 2009/0192625 A1 | 7/2009 | Boiten |
| 2009/0204229 A1 | 8/2009 | Mosley et al. |
| 2009/0204230 A1 | 8/2009 | Kaltenborn et al. |
| 2009/0204231 A1 | 8/2009 | Bonacini |
| 2009/0265018 A1 | 10/2009 | Goldfarb et al. |
| 2009/0299489 A1 | 12/2009 | Gramnaes |
| 2010/0023133 A1 | 1/2010 | Fairbanks et al. |
| 2010/0023135 A1 | 1/2010 | Rubie et al. |
| 2010/0030343 A1 | 2/2010 | Hansen et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0179668 A1 | 7/2010 | Herr et al. |
| 2010/0185301 A1 | 7/2010 | Hansen et al. |
| 2010/0241242 A1 | 9/2010 | Herr et al. |
| 2010/0262260 A1 | 10/2010 | Bédard et al. |
| 2010/0275718 A1 | 11/2010 | Stuart et al. |

(56) References Cited

U.S. PATENT DOCUMENTS

| | | |
|---|---|---|
| 2010/0305716 A1 | 12/2010 | Pusch et al. |
| 2010/0324456 A1 | 12/2010 | Jónsson et al. |
| 2010/0324699 A1 | 12/2010 | Herr et al. |
| 2010/0332002 A1 | 12/2010 | Nelson |
| 2011/0015761 A1 | 1/2011 | Celebi et al. |
| 2011/0082566 A1 | 4/2011 | Herr et al. |
| 2011/0106274 A1 | 5/2011 | Ragnarsdottir et al. |
| 2011/0125290 A1 | 5/2011 | Langlois |
| 2011/0130847 A1 | 6/2011 | Bédard et al. |
| 2011/0132131 A1 | 6/2011 | Worz |
| 2011/0137429 A1 | 6/2011 | Bédard et al. |
| 2011/0166674 A1 | 7/2011 | Montmartin |
| 2011/0196509 A1 | 8/2011 | Jansen et al. |
| 2011/0202144 A1 | 8/2011 | Palmer et al. |
| 2011/0208322 A1 | 8/2011 | Rifkin et al. |
| 2011/0224804 A1 | 9/2011 | Clausen et al. |
| 2011/0257764 A1 | 10/2011 | Herr et al. |
| 2011/0295384 A1 | 12/2011 | Herr et al. |
| 2011/0295385 A1 | 12/2011 | Herr et al. |
| 2012/0016492 A1 | 1/2012 | Clausen |
| 2012/0016493 A1 | 1/2012 | Hansen et al. |
| 2012/0078415 A1 | 3/2012 | Kubo et al. |
| 2012/0130508 A1 | 5/2012 | Harris et al. |
| 2012/0185052 A1 | 7/2012 | Lefeber |
| 2012/0191221 A1 | 7/2012 | Bédard et al. |
| 2012/0203359 A1 | 8/2012 | Schimmels et al. |
| 2012/0209405 A1 | 8/2012 | Herr et al. |
| 2012/0226364 A1 | 9/2012 | Kampas et al. |
| 2012/0259430 A1 | 10/2012 | Han et al. |
| 2012/0283845 A1 | 11/2012 | Herr et al. |
| 2012/0330439 A1 | 12/2012 | Goldfarb et al. |
| 2013/0035769 A1 | 2/2013 | Bédard et al. |
| 2013/0118287 A1 | 5/2013 | Holgate |
| 2013/0142608 A1 | 6/2013 | Zhang et al. |
| 2013/0144402 A1 | 6/2013 | Clausen et al. |
| 2013/0173022 A1 | 7/2013 | Arabian et al. |
| 2013/0197408 A1 | 8/2013 | Goldfarb et al. |
| 2013/0204395 A1 | 8/2013 | Gramnaes |
| 2013/0218295 A1 | 8/2013 | Holgate et al. |
| 2013/0218298 A1 | 8/2013 | Mosler |
| 2013/0268093 A1 | 10/2013 | Gilbert et al. |
| 2013/0282141 A1 | 10/2013 | Herr et al. |
| 2013/0297041 A1 | 11/2013 | Bédard |
| 2013/0310949 A1 | 11/2013 | Goldfarb et al. |
| 2013/0310979 A1 | 11/2013 | Herr et al. |
| 2014/0039642 A1* | 2/2014 | Nijiman .................... A61F 2/66 623/33 |
| 2014/0074243 A1 | 3/2014 | Holgate |
| 2014/0081424 A1 | 3/2014 | Herr et al. |
| 2014/0114437 A1 | 4/2014 | Herr et al. |
| 2014/0121782 A1 | 5/2014 | Herr et al. |
| 2014/0156025 A1 | 6/2014 | Bisbee, III et al. |
| 2014/0191522 A1 | 7/2014 | Birglen |
| 2014/0200680 A1 | 7/2014 | Holgate et al. |
| 2014/0277586 A1 | 9/2014 | Clausen |
| 2014/0330393 A1 | 11/2014 | Ward et al. |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0223952 A1 | 8/2015 | Langlois |
| 2015/0265429 A1 | 9/2015 | Jónsson et al. |
| 2015/0297368 A1 | 10/2015 | Langlois |
| 2015/0320573 A1 | 11/2015 | Gramnaes |
| 2015/0328020 A1 | 11/2015 | Clausen et al. |
| 2016/0158031 A1 | 6/2016 | Ward et al. |
| 2016/0158032 A1 | 6/2016 | Ward et al. |
| 2016/0302956 A1 | 10/2016 | Gilbert et al. |
| 2017/0049659 A1 | 2/2017 | Farris et al. |
| 2017/0071762 A1 | 3/2017 | Holgate et al. |
| 2017/0112640 A1 | 4/2017 | Clausen et al. |
| 2017/0241497 A1 | 8/2017 | Mooney et al. |
| 2017/0304083 A1 | 10/2017 | Clausen |
| 2017/0340504 A1 | 11/2017 | Sanz Merodio et al. |
| 2018/0125678 A1 | 5/2018 | Langlois |
| 2018/0177618 A1 | 6/2018 | Langlois |
| 2019/0175369 A1 | 6/2019 | Langlois |
| 2019/0365545 A1 | 12/2019 | Langlois |
| 2020/0000611 A1 | 1/2020 | Clausen et al. |
| 2020/0214856 A1 | 7/2020 | Hogate |
| 2020/0383804 A1 | 12/2020 | Clausen |

FOREIGN PATENT DOCUMENTS

| | | |
|---|---|---|
| CA | 2 543 061 | 6/2005 |
| CH | 543 277 | 12/1973 |
| CN | 2043873 U | 9/1989 |
| CN | 1215614 | 5/1999 |
| CN | 2400072 Y | 10/2000 |
| CN | 2776340 | 5/2006 |
| CN | 1929797 | 3/2007 |
| DE | 35 43 291 | 6/1987 |
| DE | 39 23 056 | 1/1991 |
| DE | 39 23 057 | 1/1991 |
| DE | 43 05 213 | 8/1993 |
| DE | 42 29 330 | 3/1994 |
| EP | 0 358 056 | 3/1990 |
| EP | 0 380 060 | 8/1990 |
| EP | 0 654 254 | 5/1995 |
| EP | 0 902 547 | 3/1999 |
| EP | 1 125 825 | 1/2001 |
| EP | 1 107 420 | 6/2001 |
| EP | 1 166 726 | 1/2002 |
| EP | 1 169 982 | 1/2002 |
| EP | 1 410 780 | 4/2004 |
| EP | 1 442 704 | 8/2004 |
| EP | 1 547 567 | 6/2005 |
| EP | 1 792 597 | 6/2007 |
| EP | 2 564 817 | 3/2013 |
| EP | 2 702 963 | 3/2014 |
| FR | 2 293 185 | 7/1976 |
| FR | 2 623 086 | 5/1989 |
| FR | 2 816 463 | 5/2002 |
| GB | 2 201 260 | 8/1988 |
| GB | 2 228 201 | 8/1990 |
| GB | 2 244 006 | 11/1991 |
| GB | 2 260 495 | 4/1993 |
| GB | 2 301 776 | 12/1996 |
| GB | 2 302 949 | 2/1997 |
| GB | 2 338 653 | 12/1999 |
| GB | 2 343 848 | 5/2000 |
| GB | 2 367 753 | 4/2002 |
| JP | 59-032453 | 2/1984 |
| JP | 59-071747 | 4/1984 |
| JP | 59-088572 | 5/1984 |
| JP | 59-189843 | 10/1984 |
| JP | 60-081530 | 5/1985 |
| JP | 60-177102 | 9/1985 |
| JP | 01-244748 | 9/1989 |
| JP | 03-181633 | 8/1991 |
| JP | 04-078337 | 3/1992 |
| JP | 05-123348 | 5/1993 |
| JP | 05-161668 | 6/1993 |
| JP | 07-024766 | 1/1995 |
| JP | 11-000345 | 1/1999 |
| JP | 11-056885 | 3/1999 |
| JP | 11-215793 | 8/1999 |
| JP | 2001-277175 | 10/2001 |
| JP | 2002-191654 | 7/2002 |
| JP | 2005-500 | 1/2005 |
| JP | 2005-536317 | 12/2005 |
| JP | 2009-153660 | 7/2009 |
| KR | 2002-0041137 | 6/2002 |
| SU | 1447366 | 12/1988 |
| SU | 1731210 | 5/1992 |
| WO | WO 94/006374 | 3/1994 |
| WO | WO 94/009727 | 5/1994 |
| WO | WO 95/026171 | 10/1995 |
| WO | WO 96/039110 | 12/1996 |
| WO | WO 96/041599 | 12/1996 |
| WO | WO 97/000661 | 1/1997 |
| WO | WO 97/027822 | 8/1997 |
| WO | WO 98/038951 | 9/1998 |

(56) References Cited

FOREIGN PATENT DOCUMENTS

| WO | WO 99/000075 | 1/1999 |
|---|---|---|
| WO | WO 99/005991 | 2/1999 |
| WO | WO 99/055261 | 11/1999 |
| WO | WO 00/027318 | 5/2000 |
| WO | WO 01/017466 | 3/2001 |
| WO | WO 02/080825 | 10/2002 |
| WO | WO 03/003953 | 1/2003 |
| WO | WO 03/088373 | 10/2003 |
| WO | WO 2004/017890 | 3/2004 |
| WO | WO 2004/092606 | 10/2004 |
| WO | WO 2005/048887 | 6/2005 |
| WO | WO 2005/079712 | 9/2005 |
| WO | WO 2006/076164 | 7/2006 |
| WO | WO 2007/025116 | 3/2007 |
| WO | WO 2007/095933 | 8/2007 |
| WO | WO 2008/080231 | 7/2008 |
| WO | WO 2008/080232 | 7/2008 |
| WO | WO 2008/080233 | 7/2008 |
| WO | WO 2008/080234 | 7/2008 |
| WO | WO 2010/027968 | 3/2010 |
| WO | WO 2011/005482 | 1/2011 |
| WO | WO 2011/096965 | 8/2011 |
| WO | WO 2011/100117 | 8/2011 |
| WO | WO 2011/100118 | 8/2011 |
| WO | WO 2012/062279 | 5/2012 |
| WO | WO 2012/091555 | 7/2012 |
| WO | WO 2013/006585 | 1/2013 |
| WO | WO 2013/148726 | 10/2013 |
| WO | WO 2014/133975 | 9/2014 |
| WO | WO 2015/157723 | 10/2015 |

OTHER PUBLICATIONS

Aminian et al., "Estimation of Speed and Incline of Walking Using Neural Network," IEEE Transactions on Instrumentation and Measurement, vol. 44, No. 3, Jun. 1995, pp. 743-746.

Andrews et al., "Hybrid FES Orthosis Incorporating Closed Loop Control and Sensory Feedback," Journal of Biomedical Engineering, vol. 10, Apr. 1988, pp. 189-195.

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

Au et al., "Powered Ankle-Foot Prosthesis for the Improvement of Amputee Ambulation", Proceedings of the 29th Annual International Conference of the IEEE, Aug. 23-26, 2007, p. 3020-3026.

Bachmann et al., Inertial and Magnetic Tracking of Limb Segment Orientation for Inserting Humans into Synthetic Environments, Naval Postgraduate School: Dissertation, Dec. 2000, pp. 199.

Bar et al., "Adaptive Microcomputer Control of an Artificial Knee in Level Walking," Journal of Biomechanical Engineering, vol. 5, Apr. 1983, pp. 145-150.

Baten et al., "Inertial Sensing in Ambulatory Back Load Estimation," 18th Annual International Conference of the IEEE Engineering in Medicine and Biology Society, Amsterdam, Oct. 31-Nov. 3, 1996, pp. 497-498.

Benedetti, "Gait Analysis of Patients Affected by Post-Traumatic Ankle Arthrosis Treated with Osteochondral Allograft Transplantation," SIAMOC 2006 Congress Abstracts/Gait & Posture 24S, 2006, p. S17.

Blaya, et al., "Adaptive Control of a Variable-Impedance Ankle-Foot Orthosis to Assist Drop-Foot Gait," IEEE Transactions on Neural Systems and Rehabilitation Engineering, vol. 12, No. 1, Mar. 2004, pp. 24-31.

Blaya, "Force-Controllable Ankle Foot Orthosis (AFO) to Assist Drop Foot Gait," Massachusetts Institute of Technology, Thesis, Feb. 2003 (believed to be catalogued on or after Jul. 8, 2003) in 97 pages.

Blumentritt et al., "Design Principles, Biomedical Data and Clinical Experience with A Polycentric Knee Offering Controlled Stance Phase Knee Flexion: A Preliminary Report", Journal of Prosthetics and Orthotics, vol. 9, No. 1, Winter 1997, pp. 18-24.

Bonivento et al., "Automatic Tuning of Myoelectric Prostheses", Journal of Rehabilitation Research and Development, Jul. 1998, vol. 35, No. 3, pp. 294-304.

Bortz, "A New Mathematical Formulation for Strapdown Inertial Navigation," IEEE Transactions of Aerospace and Electronic Systems, vol. AES-7, No. 1, Jan. 1971.

Bouten et al., "A Triaxial Accelerometer and Portable Data Processing Unit for the Assessment of Daily Physical Activity," IEEE Transactions on Biomedical Engineering, vol. 44, No. 3, Mar. 1997, pp. 136-147.

Bouten et al., "Assessment of Energy Expenditure for Physical Activity Using a Triaxial Accelerometer," Medicine and Science in Sports and Exercise, vol. 26, No. 12, Aug. 1994, pp. 1516-1523.

"C-Leg Fitting Statistics," Abstract, Otto Bock Orthopädische Industrie GMBH & Co., Mar. 2000, pp. 4.

Carlson et al., "Smart Prosthetics Based on Magnetorheological Fluids," 8th Annual Symposium on Smart Structures and Materials, Newport Beach, CA, Mar. 2001, pp. 9.

Carlson, J. David; "What makes a Good MR Fluid?" 8th International Conference on Electrorheological (ER) Fluids and magnetorheological (MR) Suspensions, Nice, Jul. 9-13, 2001, pp. 7.

CLAIBORNE Jr., C.J., "Making Inodes Behave,", Linux Journal, Publ. by SSC Inc, USA, Feb. 2001, No. 82, pp. 94-99.

Copes Inc., "Copes/Bionic Ankle," The Most Significant Development in Ankle Prosthetics in Over a Half Century, Brochure, Nov. 1985, pp. 3.

Crago et al., "New Control Strategies for Neuroprosthetic Systems," Journal of Rehabilitation Research and Development, vol. 33, No. 2, Apr. 1996, pp. 158-172.

Dai et al., "Application of Tilt Sensors in Functional Electrical Stimulation," IEEE Transactions on Rehabilitation Engineering, vol. 4, No. 2, Jun. 1996, pp. 63-72.

Dietl et al., "Der Einsatz von Elektronik bei Prothesen zur Versorgung der unteren Extremität," Med. Orth. Tech., 1997, vol. 117, pp. 31-35.

Diginfo TV, "Powered Prosthetic Thigh and Leg", uploaded Nov. 7, 2008 <http://www.youtube.com/watch?v=lqjtTzNEd54&feature=youtu.be%3E> [Screenshots retrieved Oct. 23, 2014 in 9 pages].

Elliott, Scott B.; "MR Microprocessor-Controlled Swing and Stance," Presentation to American Academy of Orthotists & Prosthetists (Feb. 4, 2004), 81 pages.

"Extension Spring Design Theory, Spring Rate of Extension Springs," <http://web.archive.org/web/20131209120508/http://springipedia.com/extension-design-theory.asp> as archived Dec. 9, 2013 in 1 page.

Ferrari, First in vivo Assessment of "Outwalk", A Novel Protocol for Clinical Gait Analysis Based on Inertial and Magnetic Sensors, Medical & Biological Engineering & Computing, 2010, vol. 48, pp. 1-15.

Ferris et al., An Ankle-Foot Orthosis Powered by Artificial Pneumatic Muscles, Journal of Applied Biomechanics, May 21, 2005, pp. 189-197.

Fisekovic et al., "New Controller for Functional Electrical Stimulation Systems," Medical Engineering & Physics, vol. 23, 2001, pp. 391-399.

Fite et al., "Design and Control of an Electrically Powered Knee Prosthesis", 2007 IEEE 10th International Conference on Rehabilitation Robotics, Noordwijk, The Netherlands, Jun. 12-15, 2007, pp. 902-905.

Flowers et al., "A Man-Interactive Simulator System for Above-Knee Prosthetics Studies," Massachusetts Institute of Technology, Thesis submitted—Aug. 1972, pp. 100.

Flowers et al., "An Electrohydraulic Knee-Torque Controller for a Prosthesis Simulator," Journal of Biomechanical Engineering: Transactions of the ASME; vol. 99, Series K, No. 1; Feb. 1977, pp. 3-8.

Foerster et al., "Detection of Posture and Motion by Accelerometry: A Validation Study in Ambulatory Monitoring," Computers in Human Behavior, vol. 15, 1999, pp. 571-583.

Foxlin et al., "Miniature 6-DOF Inertial System for Tracking HMDs," SPIE, vol. 3362, Apr. 13-14, 1998, pp. 15.

(56) References Cited

OTHER PUBLICATIONS

Frank et al., "Reliable Real-Time Recognition of Motion Related Human Activities Using MEMS Inertial Sensors," 2010, pp. 14, http://www.xsens.com/images/stories/PDF/Activity_Recognition_Final_ION_2010_Paper.pdf.

Fujita et al., "Joint Angle Control with Command Filter for Human Ankle Movement Using Functional Electrical Stimulation," Proceedings of the 9th Annual Conference of the IEEE Engineering in Medicine and Biology Society, Nov. 13-16, 1987, Ch. 2513, vol. 3, pp. 1719-1720.

Gard, Ph.D., Use of Quantitative Gait Analysis for the Evaluation of Prosthetic Walking Performance, Journal of Prosthetics & Orthotics, vol. 18, Issue 6, pp. P93-P104, Jan. 2006.

Gélat et al., "Adaptation of the Gait Initiation Process for Stepping on to a New Level Using a Single Step," Experimental Brain Research, vol. 133, Jun. 2000, pp. 538-546.

Godha et al., Integrated GPS/INS System for Pedestrian Navigation in a Signal Degraded Environment. ION GNSS 2006, Fort Worth TX, Sep. 26-29, 2006, p. 1-14.

Graps, Amara; "An Introduction to Wavelets," IEEE Computational Science & Engineering, vol. 2, No. 2, Summer 1995, pp. 50-61.

Grimes, Donald L., "An Active Multi-Mode Above-Knee Prosthesis Controller," Massachusetts Institute of Technology, Thesis, Jun. 1979, in 158 pages.

Grönqvist et al., "Human-Centered Approaches in Slipperiness Measurement," NIH Public Access, Author Manuscript, 2001, pp. 32. <http://www.ncbi.nlm.nih.gov/pmc/articles/PMC2895265/>.

Hanafusa et al., "A Robot Hand with Elastic Fingers and Its Application to Assembly Process," Robot Motion, Brady et al., MIT Press, Cambridge, MA, 1982, pp. 337-359.

Hanson et al., "Predicting Slips and Falls Considering Required and Available Friction," Ergonomics, vol. 42, No. 12, 1999, pp. 1619-1633.

Hashimoto et al., "An Instrumented Compliant Wrist Using a Parallel Mechanism," Japan/USA Symposium on Flexible Automation, vol. 1, ASME, 1992, pp. 741-744.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Herr et al., "User-Adaptive Control of a Magnetorheological Prosthetic Knee," Industrial Robot: An International Journal, vol. 30, No. 1, 2003. pp. 42-55.

Herr, Hugh; "Experiencing the Frontiers of Biomedical Technology," Presentation, Harvard-MIT Division of Health Sciences & Technology, Mar. 10-11, 2003, Harvard Medical School, p. 1.

Herr et al., "Patient-Adaptive Prosthetic and Orthotic Leg Systems," In Proceedings of the 12th Nordic Baltic Conference on Biomedical Engineering and Medical Physics, Jun. 18-22, 2002, pp. 18-21.

Heyn et al., "The Kinematics of the Swing Phase Obtained From Accelerometer and Gyroscope Measurements," 18th Annual International Conference of the IEEE Engineering in Medicine and Biology Society, Amsterdam 1996, pp. 463-464.

Hill et al., "Altered Kinetic Strategy for the Control of Swing Limb Elevation Over Obstacles in Unilateral Below-Knee Amputee Gait," Journal of Biomechanics, vol. 32, 1999, pp. 545-549.

Howard, Russell Duane; "Joint and Actuator Design for Enhanced Stability in Robotic Force Control," Massachusetts Institute of Technology, Thesis, Sep. 1990 (believed to be catalogued on or after Sep. 19, 1990) in 219 pages.

Jones et al., The gait initiation process in unilateral lower-limb amputees when stepping up and stepping down to a new level, Clinical Biomechanics, 2005, vol. 20, pp. 405-413 (9 pages).

Jonic et al., "Three Machine Learning Techniques for Automatic Determination of Rules to Control Locomotion," IEEE, Transactions on Biomedical Engineering, vol. 46, No. 3, Mar. 1999, pp. 300-310.

Kidder et al., "A System for the Analysis of Foot and Ankle Kinematics During Gait," IEEE Transactions on Rehabilitation Engineering, vol. 4, No. 1, Mar. 1996, pp. 25-32.

Kirkwood et al., "Automatic Detection of Gait Events: A Case Study Using Inductive Learning Techniques," Journal of Biomedical Engineering, vol. 11, Nov. 1989, pp. 511-516.

Kirsner, Scott; "A Step in the Right Direction Biomedical Horizons Expanding," Boston Globe, Mar. 17, 2003, pp. 4.

Kostov et al., "Machine Learning in Control of Functional Electrical Stimulation Systems for Locomotion," IEEE Transactions on Biomedical Engineering, vol. 42, No. 6, Jun. 1995, pp. 541-551.

Kuster et al., "Kinematic and Kinetic Comparison of Downhill and Level Walking," Clinical Biomechanics, vol. 10, No. 2, 1995, pp. 79-84.

LeFebvre, W., "Permissions and Access Control Lists", UNIX Review's Performance Computing, Publ. by Miller Freeman, USA, Oct. 1998, vol. 16, No. 11, pp. 59-61.

LaFortune, Mario A.; "Three Dimensional Acceleration of the Tibia During Walking and Running," Journal of Biomechanics, vol. 24, No. 10, 1991, pp. 877-886.

Lee et al., "Activity and Location Recognition Using Wearable Sensors," Pervasive Computing, Jul.-Sep. 2002, pp. 24-32.

Lelas et al., "Hydraulic Versus Magnetorheological-Based Electronic Knee Prostheses: A Clinical Comparison," Massachusetts, 2004, pp. 1-16.

Light et al., Skeletal Transients on Heel Strike in Normal Walking with Different Footwear, Journal of Biomechanics, vol. 13, 1980, pp. 477-480.

Luinge, H.J.; "Inertial Sensing of Human Movement," University of Twente, Netherlands, Thesis, Oct. 30, 2002 in 88 pages.

"MT9 Inertial 3D Motion Tracker," Xsens Technologies B.Y., available at http://www.xsens.com/download/MT9_brochure.pdf (at least as early as Oct. 2004), printed Jul. 20, 2006, 2 pages.

"Magnetic Fluid Improves Mobility of Prosthetic Leg", Advanced Materials & Processes, Sep. 2003, vol. 9, Issue 161, pp. 29-30, 3 pages.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to constitute prior art to U.S. Pat. No. 7,431,737 and U.S. Pat. No. 7,896,927. Applicant requests that the Examiner to consider this reference as qualifying as prior art to the present application, but reserves the right to challenge the reference's prior art status at a later date.

Martinez-Villalpando et al., "Agonist-Antagonist Active Knee Prosthesis: A Preliminary Study in Level-Ground Walking", Journal of Rehabilitation Research & Development, 2009, vol. 46, No. 3, pp. 361-373.

Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.

McNealy et al., Effect of Prosthetic Ankle Units on the Gait of Persons with Bilateral Trans-Femoral Amputations, Prosthetics and Orthotics International, 2008 32:111.

Michael, John W., M.Ed., "Upper Limb Powered Components and Controls: Current Concepts", Clinical Prosthetics and Orthotics, 1986, vol. 10, No. 2, pp. 66-77.

Michel et al., "The Strategies to Regulate and to Modulate the Propulsive Forces During Gait Initiation in Lower Limb Amputees", Experimental Brain Research, May 27, 2004, vol. 158, pp. 356-365.

Moe-Nilssen, R.; "A New Method for Evaluating Motor Control in Gait Under Real-Life Environmental Conditions. Part 1: The Instrument" Clinical Biomechanics, vol. 13, 1998, pp. 320-327.

Morris, J.R.W.; "Accelerometry-A Technique for the Measurement of Human Body Movements," Journal of Biomechanics, vol. 6, 1973, pp. 729-736.

Moseley et al., "High- and Low-Ankle Flexibility and Motor Task Performance," Gait and Posture, vol. 18, 2003, pp. 73-80.

Murray et al., "Walking Patterns of Normal Men," The Journal of Bone and Joint Surgery, vol. 46-A, No. 2, Mar. 1964.

(56) References Cited

OTHER PUBLICATIONS

Nadeau et al., "Frontal and Sagittal Plane Analyses of the Stair Climbing Task in Healthy Adults Aged Over 40 Years: What are the Challenges Compared to Level Walking?" Clinical Biomechanics, vol. 18, 2003, pp. 950-959.
Nakagawa, Akio; "Intelligent Knee Mechanism and the Possibility to Apply the Principle to the Other Joints," Proceedings of the 20th Annual International Conference of the IEEE Engineering in Medicine and Biology Society, vol. 20, No. 5, Dec. 1998, pp. 2282-2287.
Namespaces in XML, World Wide Web Consortium Working Draft 16—Sep. 1998; Tim bray (Textuality); Dave Hollander (Hewlett-Packard Company); Andrew Layman (Microsoft).
OSSUR Academy, 2004 Course Descriptions, OSSUR North America, 16 pages.
Otto Bock®, "C-LEG: A New Dimension in Amputee Mobility," Otto Bock Data Sheet, Otto Bock Orthopadische Industrie, 1997, pp. 4.
"The Electronic C-Leg® Compact Leg Prosthesis System," Instructions for Use, Otto Bock®, Otto Bock Healthcare Products GmbH, 2002, pp. 28.
Otto Bock's C-Leg, see http://web.archive.org/web/20040215152410/http:/www.ottobockus.com/products/lower_limb_prosthetics/c-leg.asp. Asserted by iWalk in Civil Action No. 12-CV-11061 FDS as known or used in this country before Jul. 15, 2004 and on sale in this country more than one year before Jul. 15, 2004. Applicant requests the Examiner to consider this reference as qualifying as prior art to the present application, but reserves the right to challenge the reference's prior art status at a later date.
"The Electronic C-Leg® Knee Joint System," Instructions for Use, Otto Bock®, 2002, pp. 30. http://www.ottobockus.com/products/lower_limb_prosthetics/c-leg_instructions.pdf (printed Jul. 20, 2006) Asserted by iWalk in Civil Action No. 12-CV-11061 FDS to constitute prior art to U.S. Patent No. 7,431,737 and U.S. Pat. No. 7,896,927. Applicant requests that the Examiner to consider this reference as qualifying as prior art to the present application, but reserves the right to challenge the reference's prior art status at a later date.
Otto Bock, Modular Knee Joints, http://www.healthcare.ottobock.com/technical_orthopedics/beinprothesen/sites/knee.htm, printed Jul. 10, 2002, 4 pages.
Otto Bock, Quality for Life, Software C-Soft, Menu-driven setting of the C-Leg, 2004 1 page.
Otto, Judith, "Prosthetic Knees: What's on the Way?" The O&P edge, http://www.oandp.com/edge/issues/articles/2003-10_02.asp, Oct. 2003, 5 pages.
Otto, Judith, "Prosthetic Knees: What's Currently New and Impressive?", The O&P Edge, http://www.oandp.com/edge/issues/articles/2003-10_03.asp, Oct. 2003, 4 pages.
Perry, Jacquelin MD, "Gait Analysis: Normal and Pathological Function," Ch. 4, pp. 51-53, 85-87, 1992.
Perry, Jacquelin MD, "Gait Analysis: Normal and Pathological Function," Ch. 5, pp. 92-108, 1992.
Perry, Jacquelin MD, "Gait Analysis: Normal and Pathological Function," Entire Book, 1992.
Petrofsky et al., "Feedback Control System for Walking in Man," Computers in Biology and Medicine, vol. 14, No. 2, pp. 135-149, 1984.
Pfeffer et al., "Experiments with a Dual-Armed, Cooperative, Flexible-Drivetrain Robot System," Proceedings of 1993 IEEE International Conference on Robotics and Automation, vol. 3, May 5, 1993, pp. 601-608.
Popovic et al., "Control Aspects of Active Above-Knee Prosthesis," International Journal of Man-Machine Studies, vol. 35, No. 6, Dec. 1991, pp. 751-767.
Popovic et al., "Optimal Control for an Above-Knee Prosthesis With Two Degrees of Freedom," Journal of Biomechanics, vol. 28, No. 1, 1995, pp. 89-98.
Powers et al., Stair Ambulation in Persons with Transtibial Amputation: An Analysis of the Seattle LightFoot™, Journal of Rehabilitation Research and Development, vol. 34, No. 1, Jan. 1997, pp. 9-18.
Proteor, "Assembly and Adjustment Instructions for IP50-R," Sep. 2004, pp. 1-21.
Raggi et al., Gait Analysis Through Inertial Sensors in Transfemoral Amputees: Step and Stride Regularity, SIAMOC 2006 Congress Abstracts/Gait & Posture.
Raggi et al. Wearable Sensors for the Real-Time Assessment of Gait Temporal Symmetry in Above-Knee Amputees: The 'SEAG' Protocol, Abstracts of the 2007 SIAMOC Congress.
Rao et al., "Segment Velocities in Normal and Transtibial Amputees: Prosthetic Design Implications," IEEE Transactions on Rehabilitation Engineering, vol. 6, No. 2, Jun. 1998, pp. 219-226.
Rapport De Recherche Europeenne EP 01169982, mailed on Nov. 6, 2001.
Redfern et al., "Biomechanics of Descending Ramps," Gait and Posture, vol. 6, 1997, pp. 119-125.
Reitman et al., "Gait Analysis in Prosthetics: Opinions, Ideas, and Conclusions," Prosthetics and Orthotics International, vol. 26, 2002, 50-57.
Riener et al., "Stair Ascent and Descent at Different Inclinations," Gait and Posture, vol. 15, 2002, pp. 32-44.
Robinson, David William; "Design and Analysis of Series Elasticity in Closed-Loop Actuator Force Control," Massachusetts Institute of Technology, Thesis, Jun. 2000 in 123 pages.
Robinson et al., "Series Elastic Actuator Development for a Biomimetic Walking Robot," MIT Leg Laboratory, 1999, pp. 1-8.
Schmalz et al., "Energy Efficiency of Trans-Femoral Amputees Walking on Computer-Controlled Prosthetic Knee Joint 'C-Leg,'" International Society for Prosthetics and Orthotics: Conference Book 9th World ISPO-World Congress, 1998, pp. 3.
Sekine et al., "Classification of Waist-Acceleration Signals in a Continuous Walking Record," Medical Engineering & Physics, 2000, pp. 285-291.
Sin et al., "Significance of Non-Level Walking on Transtibial Prosthesis Fitting with Particular Reference to the Effects of Anterior-Posterior Alignment," Journal of Rehabilitation Research and Development, vol. 38, No. 1, Jan./Feb. 2001, pp. 1-6.
Smidt et al., "An Automated Accelerometry System for Gait Analysis," Journal of Biomechanics, vol. 10, 1977, pp. 367-375.
Sowell et al., "A Preliminary Clinical Evaluation of the Mauch Hydraulic Foot-Ankle System," Prosthetics and Orthotics International, vol. 5, 1981, pp. 87-91.
"State-of-the-Art Prosthetic Leg Incorporates Magneto-Rheological Technology," Medical Product Manufacturing News, Nov. 2000, p. 42 [Web version attached in 3 pages].
Su et al., The Effects of Increased Prosthetic Ankle Motions on the Gait of Persons with Bilateral Transtibial Amputations, Am. J. Phys. Med. Rehabil., vol. 89, No. 1, Jan. 2010.
Suga et al., "Newly Designed Computer Controlled Knee-Ankle-Foot Orthosis (Intelligent Orthosis)", Prosthetics and Orthotics International, vol. 22, 1998, pp. 230-239.
Sugano et al., "Force Control of the Robot Finger Joint Equipped with Mechanical Compliance Adjuster," Proceedings of the 1992 IEEE/RSJ International Conference on Intelligent Robots & Systems, Jul. 7-10, 1992, pp. 2005-2013.
Sup et al., "Design and Control of an Active Electrical Knee and Ankle Prosthesis", Proceedings of the 2nd Biennial IEEE/RASEMBS International Conference on biomedical Robotics and Biomechatronics, Scottsdale, AZ, Oct. 19-22, 2008, pp. 523-528.
Sup et al., "Design and Control of a Powered Knee and Ankle Prosthesis", 2007 IEEE International Conference on Robotics and Automation, Rome, Italy, Apr. 10, 2007, pp. 4134-4139.
Sup et al., "Design and Control of a Powered Transfemoral Prosthesis", The International Journal of Robotics Research, Feb. 2008, vol. 27, pp. 263-273.
Sup et al., "Design of a Pneumatically Actuated Transfemoral Prosthesis", Proceedings of IMECE2006: 2006 ASME International mechanical Engineering Congress and Exposition, Chicago, Illinois, Nov. 5-10, 2006, pp. 1-10.

(56) References Cited

OTHER PUBLICATIONS

Thakkar, Sneha, "Energy Economy Gait Analysis of an Autoadaptive Prosthetic Knee," Massachusetts Institute of Technology, Thesis, Aug. 30, 2002 in 58 pages.
Tomović et al., "A Finite State Approach to the Synthesis of Bioengineering Control Systems," IEEE Transactions of Human Factors in Electronics, vol. HFE-7, No. 2, Jun. 1966, pp. 65-69.
Tong et al., "A Practical Gait Analysis System Using Gyroscopes," Medical Engineering and Physics, vol. 21, 1999, pp. 87-94.
Tong et al., "Virtual Artificial Sensor Technique for Functional Electrical Stimulation," Medical Engineering & Physics, vol. 20, 1998, pp. 458-468.
Townsend et al., "Biomechanics and Modeling of Bipedal Climbing and Descending," Journal of Biomechanics, vol. 9, No. 4, 1976, pp. 227-239.
Van Den Bogert et al., "A Method for Inverse Dynamic Analysis Using Accelerometry," Journal of Biomechanics, vol. 29, No. 7, 1996, pp. 949-954.
Van Der Kooij et al., "A Multisensory Integration Model of Human Stance Control," Biological Cybernetics, vol. 80, pp. 299-308, 1998.
Van Der Loos et al., "ProVAR Assistive Robot System Architecture," Proceedings of the 1999 IEEE International Conference on Robotics & Automation, Detroit, Michigan, vol. 1, May 1999, pp. 741-746.
Varol et al., "Decomposition-Based Control for a Powered Knee and Ankle Transfemoral Prosthesis", Proceedings of the 2007 IEEE IOth International Conference on Rehabilitation Robotics, Noordwijk, The Netherlands, Jun. 12-15, 2007, pp. 783-789.
Varol et al., "Real-time Gait Mode Intent Recognition of a Powered Knee and Ankle Prosthesis for Standing and Walking", Proceedings of the 2nd Biennial IEEE/RAS-EMBS International Conference on Biomedical Robotics and Biomechatronics, Scottsdale, AZ, Oct. 19-22, 2008, pp. 66-72.
Varol et al., "Real-time Intent Recognition for a Powered Knee and Ankle Transfemoral Prosthesis", Proceedings of the 2007 IEEE 10th International Conference on Rehabilitation Robotics, Noordwijk, The Netherlands, Jun. 12-15, 2007, pp. 16-23.
Veltink et al., "Detection of Static and Dynamic Activities using Uniaxial Accelerometers," IEEE Transactions on Rehabilitation Engineering, vol. 4, No. 4, Dec. 1996, pp. 375-385.
Veltink et al., "The Feasibility of Posture and Movement Detection by Accelerometry," 15th Annual International Conference of the IEEE Engineering in Medicine and Biology Society, Oct. 28-31, 1993, San Diego, California, pp. 1230-1231.
Wilkenfeld, Ari J, Ph.D.; "An Auto-Adaptive External Knee Prosthesis," Artificial Intelligence Laboratory, MIT, Sep. 2000, pp. 3.
Wilkenfeld, Ari J, Ph.D.; "Biologically Inspired Autoadaptive Control of a Knee Prosthesis," Massachusetts Institute of Technology, Thesis, Jul. 2000, (believed to be catalogued on or after Oct. 23, 2000) in 106 pages.
Willemsen et al., "Automatic Stance-Swing Phase Detection from Accelerometer Data for Peroneal Nerve Stimulation," IEEE Transactions on Biomedical Engineering, vol. 37, No. 12, Dec. 1990, pp. 1201-1208.
Willemsen et al., "Real-Time Gait Assessment Utilizing a New Way of Accelerometry," Journal of Biomechanics, vol. 23, No. 8, 1990. pp. 859-863.
Williamson, Matthew M.; "Series Elastic Actuators," Massachusetts Institute of Technology Artificial Intelligence Laboratory, A.I. Technical Report No. 1524, Jan. 1995, pp. 1-83.
Woodward et al., "Skeletal Accelerations Measured During Different Exercises," Proceedings of the Institution of Mechanical Engineers, Part H, Journal of Engineering in Medicine, vol. 207, No. 2, Jun. 1993, pp. 79-85.
Wu et al., "The Study of Kinematic Transients in Locomotion Using the Integrated Kinematic Sensor," IEEE Transactions on Rehabilitation Engineering, vol. 4, No. 3, Sep. 1996, pp. 193-200.
Zamiska, Nicholas, "Bionic Knee 'Learns' How to Walk", The Wall Street Journal, Jul. 6, 2004, pp. 1.
International Search Report and Written Opinion in International Application No. PCT/US2013/026285 dated Jun. 19, 2013 in 4 pages.
International Search Report and Written Opinion in International Application No. PCT/US2014/061913 dated Feb. 5, 2015 in 8 pages.
International Search Report and Written Opinion in PCT Application No. PCT/US2014/22013, dated Aug. 27, 2014.
Official Communication in Chinese Application No. 201380042111.2, dated May 27, 2016.
International Search Report and Written Opinion in PCT Application No. PCT/US2014/018086, dated May 9, 2014.
International Preliminary Report on Patentability and Written Opinion in PCT Application No. PCT/US2014/018086, dated Sep. 11, 2015.
International Search Report and Written Opinion in PCT Application No. PCT/US2013/033937, dated Jun. 7, 2013.
International Search Report and Written Opinion in Application No. PCT/IB2012/000998, dated Sep. 11, 2012.

* cited by examiner

PROSTHETIC FOOT WITH ENHANCED STABILITY AND ELASTIC ENERGY RETURN

CROSS-REFERENCE TO RELATED APPLICATIONS

This application is a continuation of U.S. application Ser. No. 16/374,055, filed Apr. 3, 2019, now U.S. Pat. No. 11,285,024, which is a continuation of U.S. application Ser. No. 15/386,366, filed Dec. 21, 2016, now U.S. Pat. No. 10,369,019, which is a continuation of U.S. application Ser. No. 14/188,216, filed Feb. 24, 2014, now U.S. Pat. No. 9,561,118, which claims priority benefit of U.S. Provisional Application Nos. 61/769,405, filed Feb. 26, 2013 and 61/770,212, filed Feb. 27, 2013, the entirety of each of which are hereby incorporated by reference herein and should be considered a part of this specification.

BACKGROUND

Field

The present application relates to prosthetic feet and other prosthetic devices including a spring, and more particularly to prosthetic feet and other prosthetic devices having one or more flexible members between two or more joints (e.g., pivots) and allowing for variable stiffness during use.

Description of the Related Art

In the field of prosthetics, particularly prosthetic feet, it is desirable to provide a high level of functionality with reliable performance. Further, as each user is different, it is desirable to provide a prosthesis that can be adapted to the particular needs of each individual user.

SUMMARY

Particularly in the area of prosthetic feet, it is desirable to provide a prosthesis that provides stability throughout the gait cycle and in other activities such as stance. Further, during movement it is often desirable for a prosthetic foot to absorb and return elastic energy, while having enhanced energy conservation during ambulation. Even further, it is desirable for a prosthetic foot to be adjustable to an individual who may have various weights, heights, stride lengths, etc., as well as for prosthetic foot designs to allow for a variable stiffness, depending on the activity level of the amputee.

In accordance with one embodiment, a prosthetic foot is provided having one or more flexible members between two or more joints (e.g., pivots) to provide improved control and stability during a stance phase of gait cycle (e.g., provide more movement during stance). In one embodiment, the prosthetic foot is purely a mechanical foot. In another embodiment the prosthetic foot can include an actuator. In some embodiments, the actuator can be an active actuator (e.g., an electric motor) that can be selectively actuated (e.g., via an electric controller) to impart mechanical motion to the prosthetic foot (e.g., to change the orientation of the prosthetic ankle during a swing phase of gait cycle to dorsiflexion and then to plantarflexion). In another embodiment, the actuator can be a passive actuator (e.g., resilient member, spring or stiff beam).

In another embodiment, a prosthetic foot is provided with a variable stiffness control, which allows the stiffness of the prosthetic foot to be adjusted for different types of gait. In some embodiments, the variable stiffness control is mechanically actuatable (e.g., actuated manually by a user) to vary the stiffness of one or more elastic elements of the prosthetic foot (e.g., by changing the length of a lever arm of an elastic element, or by varying a gap between adjacent elastic elements). In another embodiment, the variable stiffness control can be automatically or actively adjusted during ambulation by the user (e.g., automatic adjustment of a lever arm of an elastic element, or active varying of a gap between adjacent elastic elements), e.g., based on the activity level of the user or the phase of gait cycle. In some embodiments the variable stiffness control can be automatically adjusted based on a sensed parameter of gait (e.g., sensed with one or more sensors on the prosthetic device).

In still another embodiment, the prosthetic foot or device can include a housing or adapter (e.g., for coupling the prosthetic foot or device to another prosthetic component) with a mechanism that provides for flexible motion in one or more planes (e.g., sagittal, coronal, transverse) so as to allow motion of the housing or adapter in a medial-lateral, anterior-posterior, or torsional direction. In one embodiment, where the prosthetic device is a prosthetic foot, the housing or adapter can be located generally at a location associated with a natural human ankle, and provide for motion similar to that of a natural human ankle. In some embodiments, the mechanism can include one or more slots or openings in one or more surfaces of the housing or adapter (e.g., slots on medial and lateral surfaces of the housing or adapter), that movably receive one or more pins, axles or joint members that connect the housing or adapter with other components (e.g., elastic elements or foot plates) of the prosthetic foot.

In one embodiment, a prosthetic foot comprises an attachment member and two or more flexible members. The attachment member can include a connector configured to connect the attachment member to a user or another prosthetic device. The two or more flexible members can be rotatably attached to the attachment member by rotatable joints such that the flexible members can both rotate and flex relative to the attachment member when the prosthetic foot contacts the ground.

In another embodiment, a prosthetic foot can include an attachment member, two or more flexible members, and an adjustable fastening member. The attachment member can include a connector configured to connect the attachment member to a user or another prosthetic device. The two or more flexible members can attach to the attachment member. Further, the two or more flexible members can extend from the attachment member to a foot portion of the prosthetic foot and be substantially movable relative to each other along their lengths. The adjustable fastening member can be configured to fasten the two or more flexible members along the foot portion of the prosthetic foot. Further, fastening can be provided at a plurality of positions along the length of the two or more flexible members to change the flexibility and resistance of the two or more flexible members.

In further embodiments, a prosthetic foot can include an attachment member, two or more flexible members, and a variable stiffness control member. The attachment member can include a connector configured to connect the attachment member to a user or another prosthetic device. The two or more flexible members can attach to the attachment member and can extend from the attachment member to a foot portion of the prosthetic foot. The flexible members can be substantially movable relative to each other along their lengths. However, the variable stiffness control member can be configured to adjust a length of a lever arm of the two or more flexible members along the foot portion of the prosthetic foot. For example, the variable stiffness control member can limit the relative motion between the flexible members.

In further embodiments, a prosthetic foot can include one or more flexible foot plates, an attachment member, and a means for modifying the stiffness of the prosthetic foot. The one or more flexible foot plates can be configured to bend along their lengths. The attachment member can include a connector configured to connect the attachment member to a user or another prosthetic device. The means for modifying the stiffness of the prosthetic foot can change the bending length of one or more of the flexible foot plates either prior to or during use.

In further embodiments, a prosthetic foot can include one or more elastic elements and an attachment member. The one or more elastic elements can be configured to bend along their lengths. The attachment member can include a connector configured to connect the attachment member to a user or another prosthetic device. Further, the attachment adapter can be connected to the one or more elastic elements via at least two pivotable joints. At least one of the elastic elements can extend between the at least two pivotable joints.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION

FIGS. 1-8 depict an embodiment of a prosthetic foot 1. The prosthetic foot 1 can attach to a user or to another prosthetic device with an attachment member 10. The attachment member 10 is depicted as including a first connection portion 12 shown as a pyramid connector. The pyramid connector can attach to a stump on a user, to another prosthetic device, or to any other appropriate object. Further, it will be understood that the first connection portion 12 can include attachment features other than a pyramid connector, such as a threaded hole or screw, a latch, a magnetic member, tube clamp, or other features.

Figure 4:
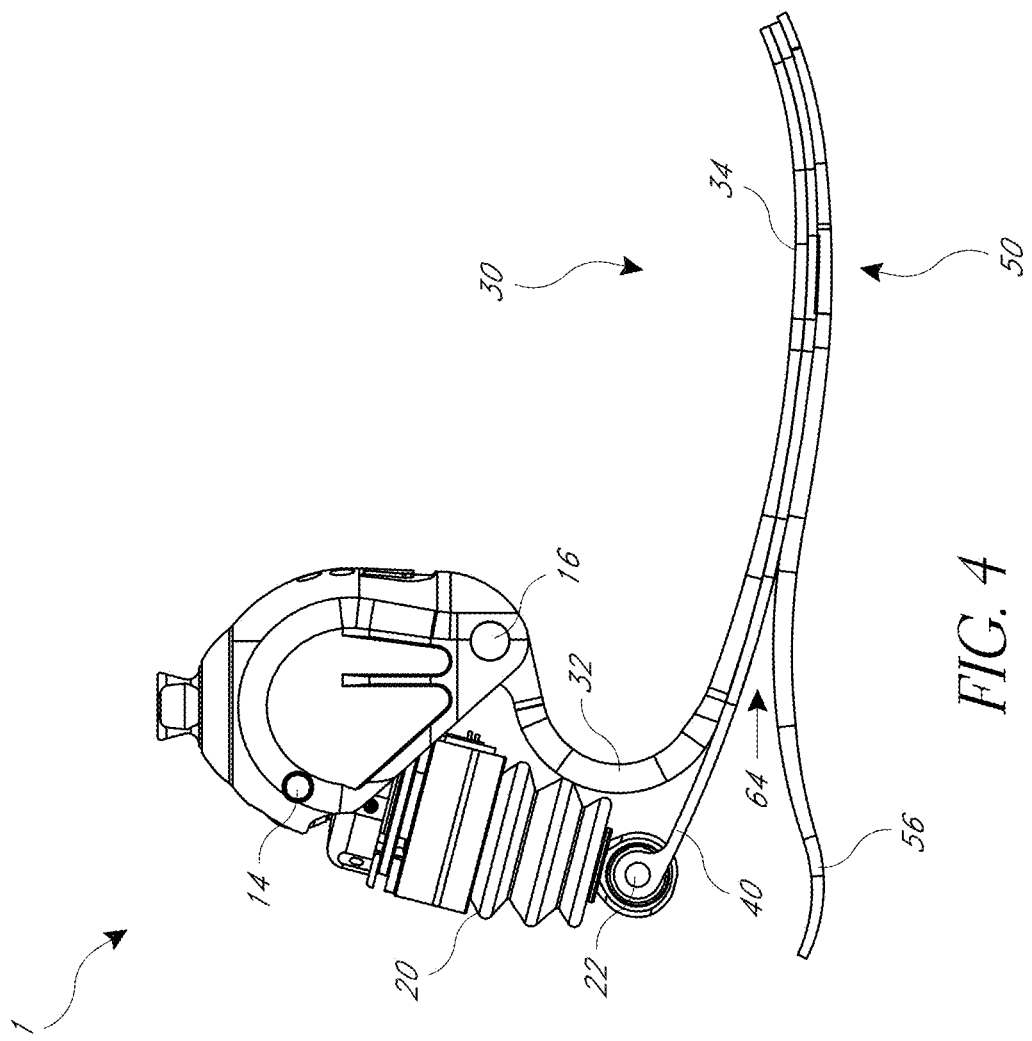
FIG. 4 is a side view of the prosthetic foot of FIG. 1.
Figure 7:
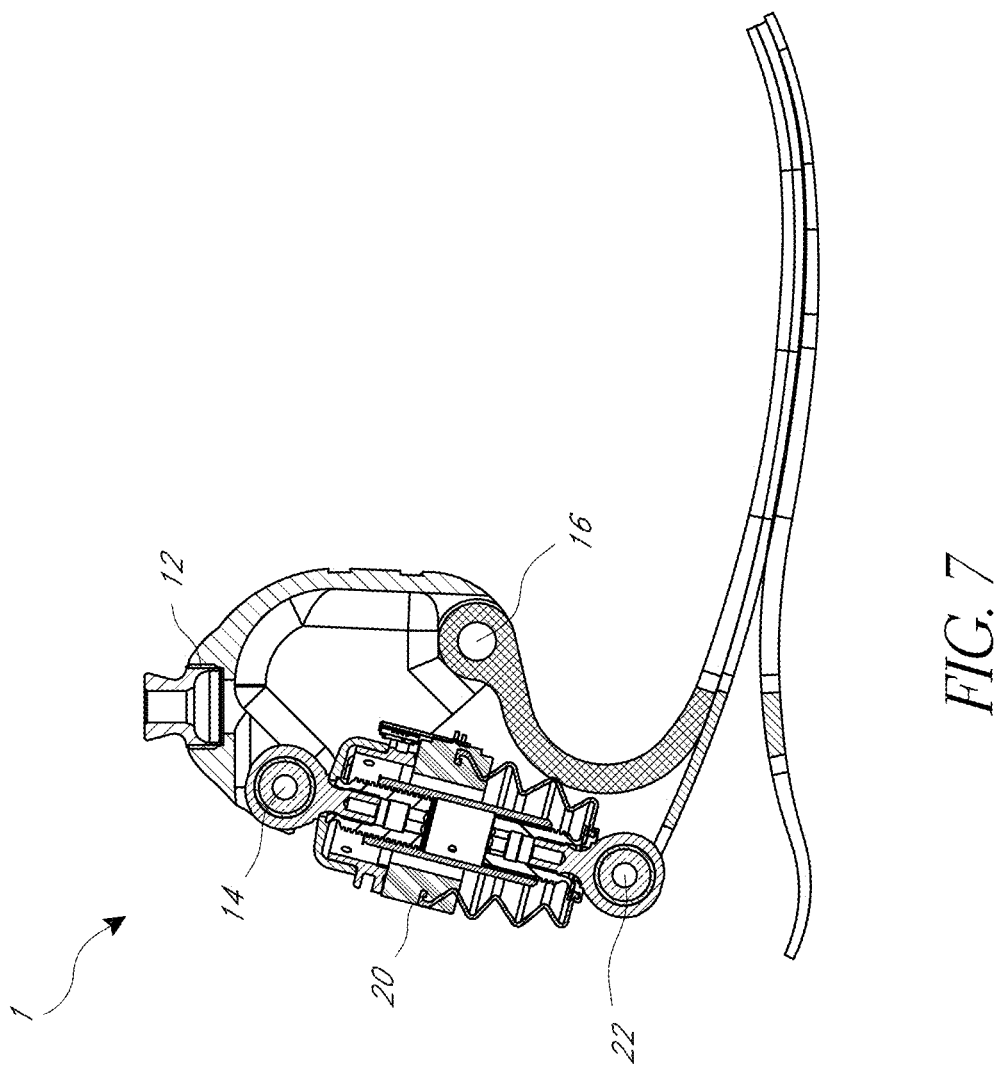
FIG. 7 is a cross-sectional side view of the prosthetic foot of FIG. 1.

The attachment member 10 can additionally include second and third connection portions 14, 16 (see FIGS. 4, 7). The attachment member 10 can serve to provide a rigid connection between the connection portions 12, 14, 16. For example, the attachment member 10 can comprise a substantially rigid material such as aluminum, steel, titanium, other metals or metallic alloys, carbon fiber, composites, or substantially rigid plastics. However, in other embodiments the attachment member 10 can be configured to provide flexibility, potentially in multiple planes. Thus, in some embodiments the attachment member 10 can comprise a more flexible material or include flexible joints between separate components of the attachment member 10. For example, in some embodiments the attachment member 10 can have a flexible connection with the first connection portion 12, allowing for motion in the medial/lateral and/or anterior/posterior directions. Further, the connection may allow torsional flexibility with the first connection portion 12. In other embodiments, as further described below, the attachment member 10 can have a flexible connection with one or both of the second and third connection portions 14, 16.

Further, in some embodiments the attachment member 10 can include other features of a prosthetic foot such as sensors configured to measure, for example, the position and movement of the prosthetic foot, the position and movement of various joints and components on the prosthetic foot (such as the rotational position and movement at the connection portions 14, 16 and an actuator 20, as further discussed below), pressures and forces on various components of the prosthetic foot 1 (such as on the attachment member 10, the actuator 20, or the elastic members 30, 40, 50, further discussed below), and other measurable characteristics of the prosthetic foot. The sensors can additionally be configured to measure the prosthetic foot's environment, such as a terrain on which the prosthetic foot 1 moves. It will be understood that these sensors can be positioned on other elements of the prosthetic foot 1, such as the actuator 20, the elastic members 30, 40, 50, and other elements, further described below.

The attachment member 10 can also include electronics (e.g., computer processor). For example, the attachment member 10 can include electronics configured to receive information from the sensors, discussed above. Further, in some embodiments, the attachment member 10 can include electronics configured to communicate information (e.g., information from the sensors) to other electronic devices, such as to other prosthetic devices or to an external computer (e.g., via wired or wireless communication, such as RF communication). Such electronics may also be configured to receive information from other prosthetic devices or an external computer, such information potentially including information from other sensors and/or operational commands for the prosthetic foot 1.

The attachment member 10 can additionally include or define a cover 18. The cover 18 can protect various components of the prosthetic foot 1 such as electronics (as described above), the actuator 20 (describe below), or other components. In some embodiments the cover 18 can include open portions in the coronal plane, allowing flexibility of motion in the medial-lateral directions. In further embodiments the cover 18 can include open portions in the sagittal plane, allowing flexibility of motion in the anterior-posterior directions. In some embodiments, the open portions can be vertical or horizontal slots formed in the cover 18, to allow movement of pivot axles associated with any one of the connection portions 12, 14, 16.

Figure 1:
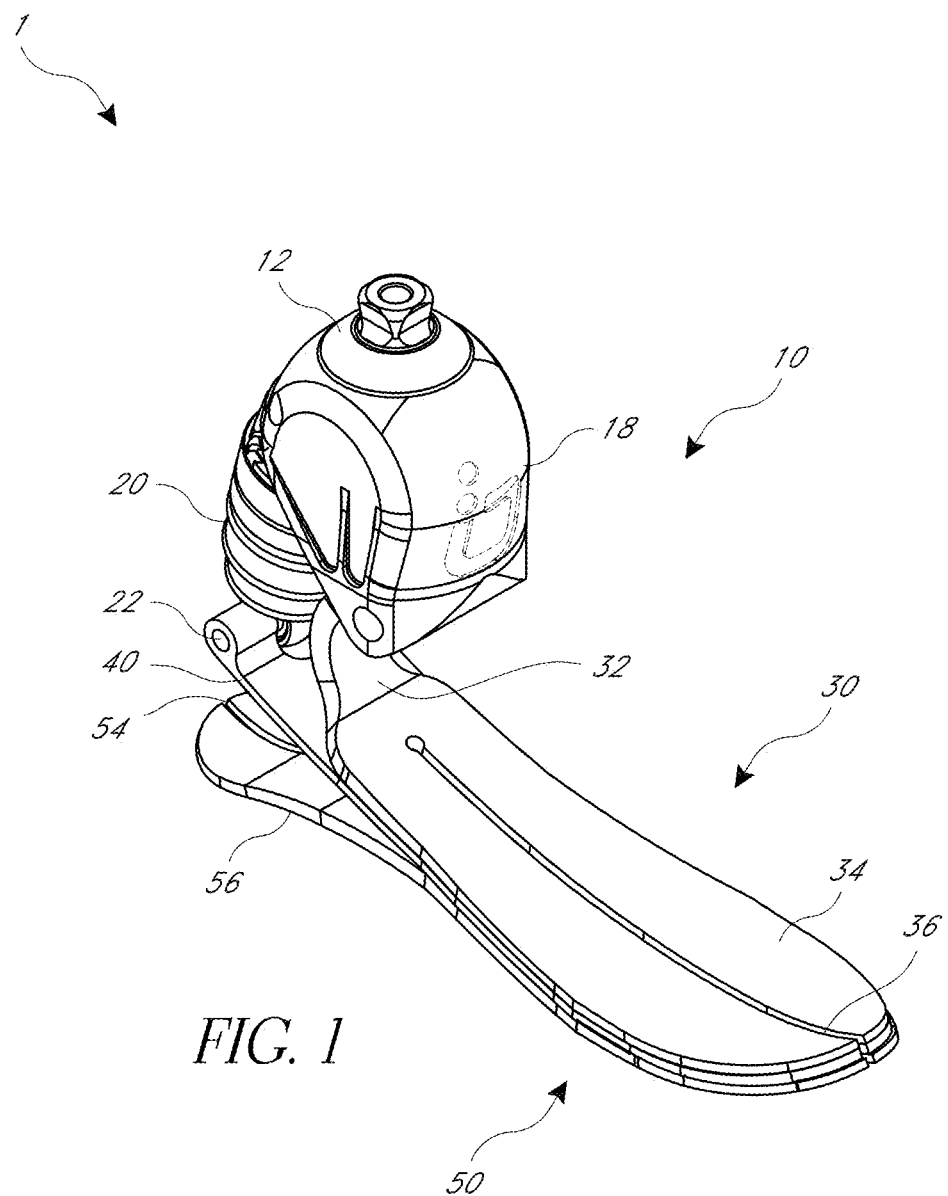
FIG. 1 is a perspective view of an embodiment of a prosthetic foot.
Figure 3:
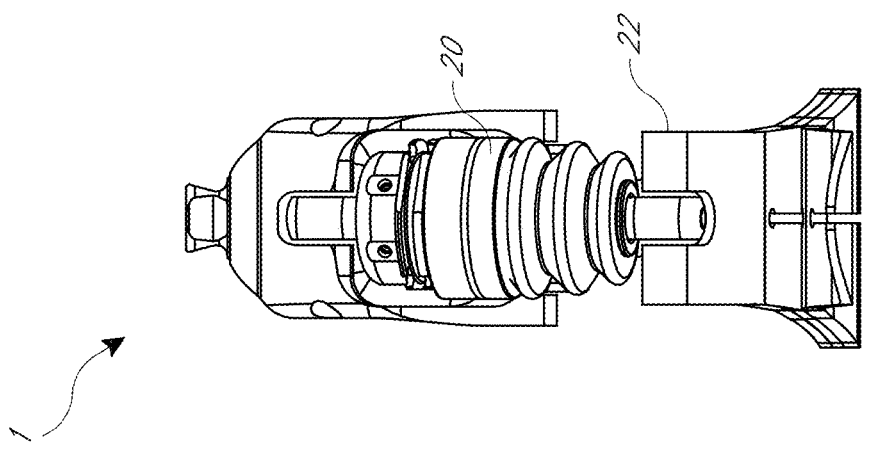
FIG. 3 is a rear view of the prosthetic foot of FIG. 1.
Figure 2:
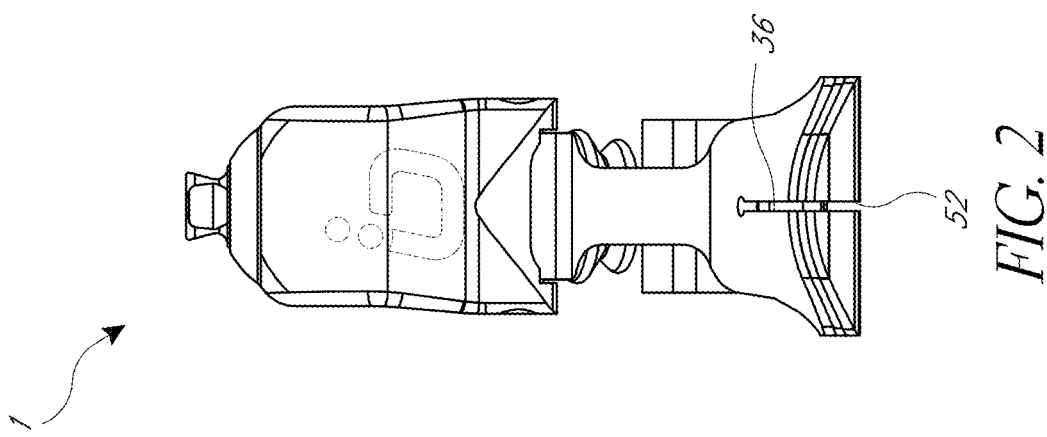
FIG. 2 is a front view of the prosthetic foot of FIG. 1.

As shown in FIG. 1, the attachment member 10 can connect to a first elastic member 30 at the third connection portion 16. In some embodiments the third connection portion 16 can provide a rotatable connection, although non-rotatable connections can also be used. In some embodiments, the rotation can be provided by an axle firmly mounted to the attachment member 10, about which the first elastic member 30 can rotate. In other embodiments, the first elastic member 30 can be fixed to the axle, and relative rotation can be allowed between the axle and the attachment member 30. In one embodiment, the first elastic member 30 can include or define a bushing or opening through which the axle extends. The first elastic member 30 can be formed from a sufficiently flexible material such as carbon fiber, though other suitable materials or combination of materials can be used (e.g., carbon and glass fibers). In other embodiments, the first elastic member 30 can be substantially inelastic, so as to provide a rigid connection. It will be understood that the other elastic members 40, 50 (described further below) can be formed of similar materials and have similar connections as the first elastic member 30.

Further, the first elastic member 30 can be formed into a shape configured to provide a desired flexibility or rigidity. As shown in FIG. 1, the elastic member 30 includes a C-shaped portion 32 at an upper portion (proximal portion) of the first elastic member, near the third connection portion 16. The C-shaped portion 32 is depicted as including an opening facing forward (e.g., the C-shaped portion 32 curves forwardly so that it is concave toward the front of the prosthetic foot), although in other embodiments the C-shaped portion can have an opening facing backward (e.g., the C-shaped portion can curve rearwardly so that it is concave toward the rear of the prosthetic foot). In some embodiments, the C-shaped portion 32 can bend more than 90 degrees, more than 110 degrees, 130 degrees, 150 degrees, or 170 degrees when unloaded. The bend of the C-shaped portion 32 can affect the resistance or flexibility of the first elastic member 30. Notably, this resistance or flexibility can be adjusted, as described further below.

In the embodiment of FIG. 1, the elastic member 30 can extend from the lower portion of the C-shaped portion 32 into a foot portion 34. The foot portion 34 of the elastic member 30 can be substantially flat and extend from a rear portion of the prosthetic foot 1 toward a toe region of the prosthetic foot 1. The foot portion 34 can further include a slit 36. As shown, the slit 36 extends longitudinally to a toe end of the elastic member 30 to separate the foot portion 34 into two or more foot members that can flex independently, although in some embodiments the slit 36 can be closed at the toe end (e.g., where at least one of the elastic members 30, 40, 50 are solid at a toe portion such that the slit terminates prior to the end of the at least one elastic member). As will be discussed further below, the slit 34 can allow the flexibility and resistance of the elastic member 30 to be altered. In another embodiment, the elastic members 30, 40, 50 can be monolithic without any slits.

As further shown in FIG. 4, the attachment member 10 can connect to an actuator 20 at the second connection portion 14. Like the third connection portion 16, the second connection portion 14 can be rotatable or non-rotatable. Notably, in FIG. 4 the third connection portion 16 is in a front portion of the attachment member 10, and the second connection portion 14 is in a rear portion of the attachment member 10. Similarly, the actuator 20 is located at a rear portion of the prosthetic foot 1. However, in other embodiments the actuator 20 can be positioned in a front portion of the prosthetic foot 1, as further described below.

The actuator 20 can be in a variety of forms and can be operated in a variety of ways, as described by way of example in U.S. patent application Ser. No. 11/367,049, issued Mar. 1, 2011 as U.S. Pat. No. 7,896,927, and U.S. patent application Ser. No. 12/816,968, published as U.S. 2010/0324698 on Dec. 23, 2010, both of which are incorporated herein by reference and should be considered a part of this specification. For example, the actuator 20 can be a powered actuator such as a screw motor, or a passive member such as an elastic member (e.g., a spring) or a chamber with a magnetorheologic fluid, or can be a hydraulic or pneumatic system. Further, the actuator 20 can be configured to operate in a variety of ways, as also discussed in U.S. Pat. No. 7,896,927 and US 2010/0324698. For example, the actuator 20 can be configured to extend or contract to assist a user during a gait cycle. For example, the actuator 20 can change the orientation of the prosthetic foot 1 to dorsiflexion and then to plantarflexion during a swing phase of gait cycle so that the toe portion of the prosthetic foot 1 is raised during the initial portion of swing phase. In another embodiment, the actuator 20 can change the orientation of the prosthetic foot 1 to plantarflexion when the user is in a relaxed (e.g., sitting) position. Further, such motion of the actuator 20 can change the flexibility or resistance of the elastic members 30, 40, 50, as further described below. In some embodiments, the actuator 20 can also enter a low power mode (e.g., hibernation mode), such as a relaxed mode or an inactive mode. For example, the actuator 20 may enter a low power mode during stance, as the embodiments described herein can provide greater stability during stance, as further described below. Advantageously, the low power mode allows for the conservation of battery power used to power the actuator 20, allowing the actuator 20 to be operated for longer periods of time between battery charging.

Figure 4A:
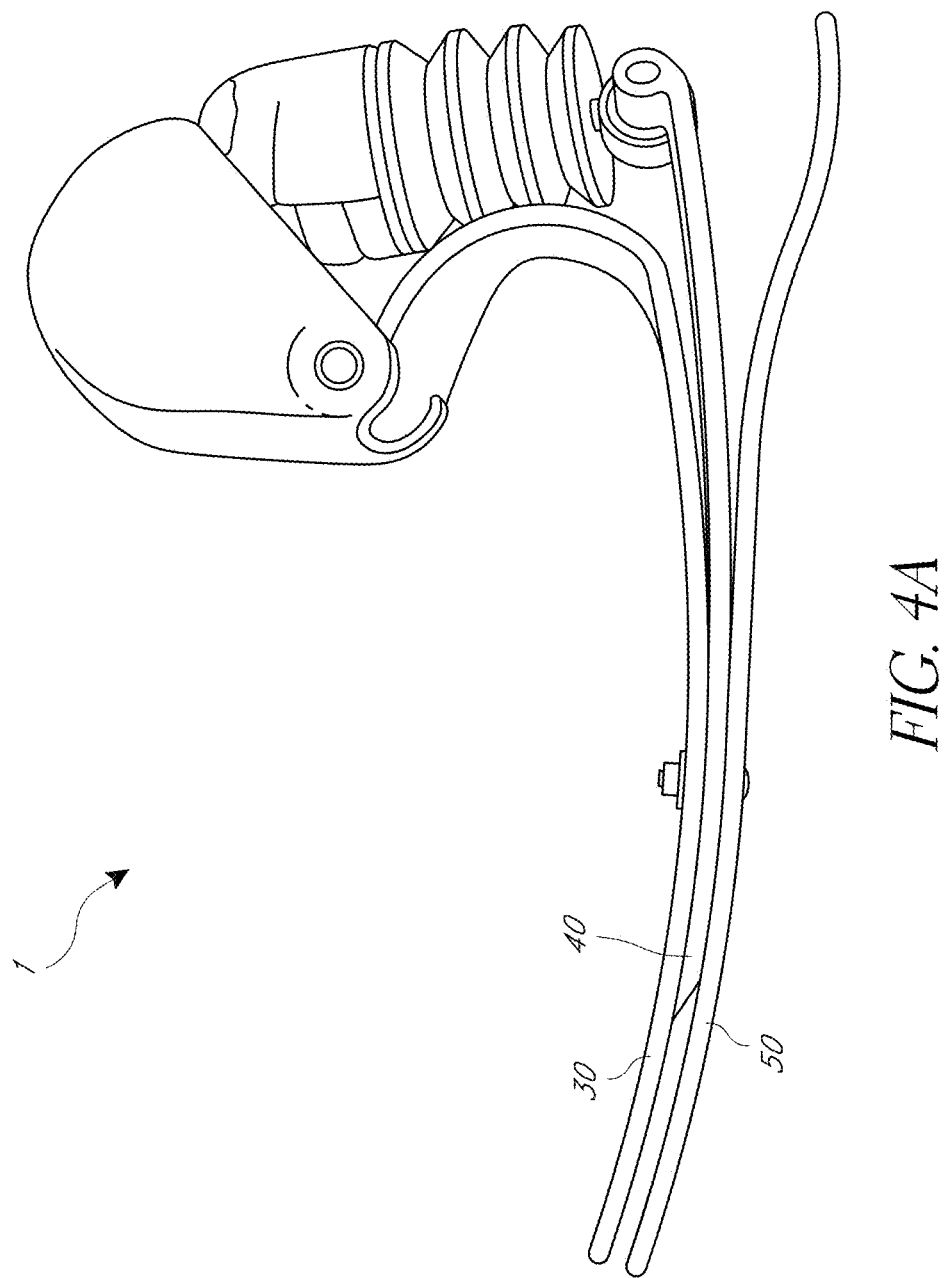
FIG. 4A is a side view of another embodiment of a prosthetic foot, similar to the prosthetic foot of FIG. 1.
Figure 5:
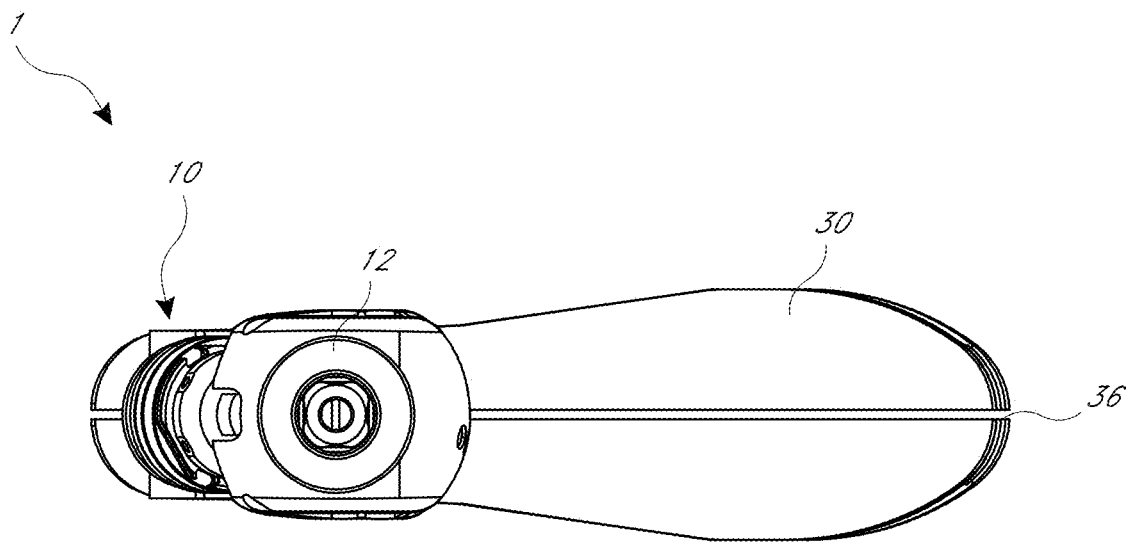
FIG. 5 is a top view of the prosthetic foot of FIG. 1.
Figure 6:
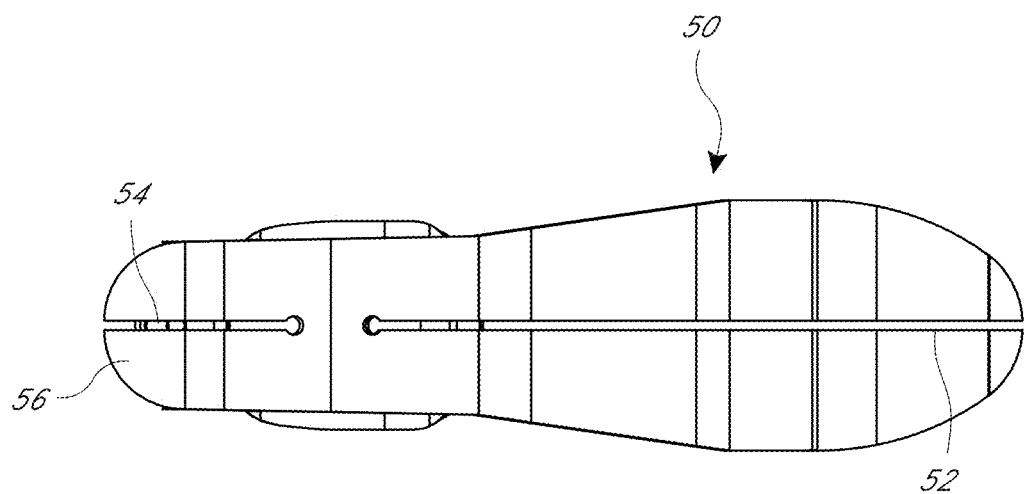
FIG. 6 is a bottom view of the prosthetic foot of FIG. 1.
Figure 8:
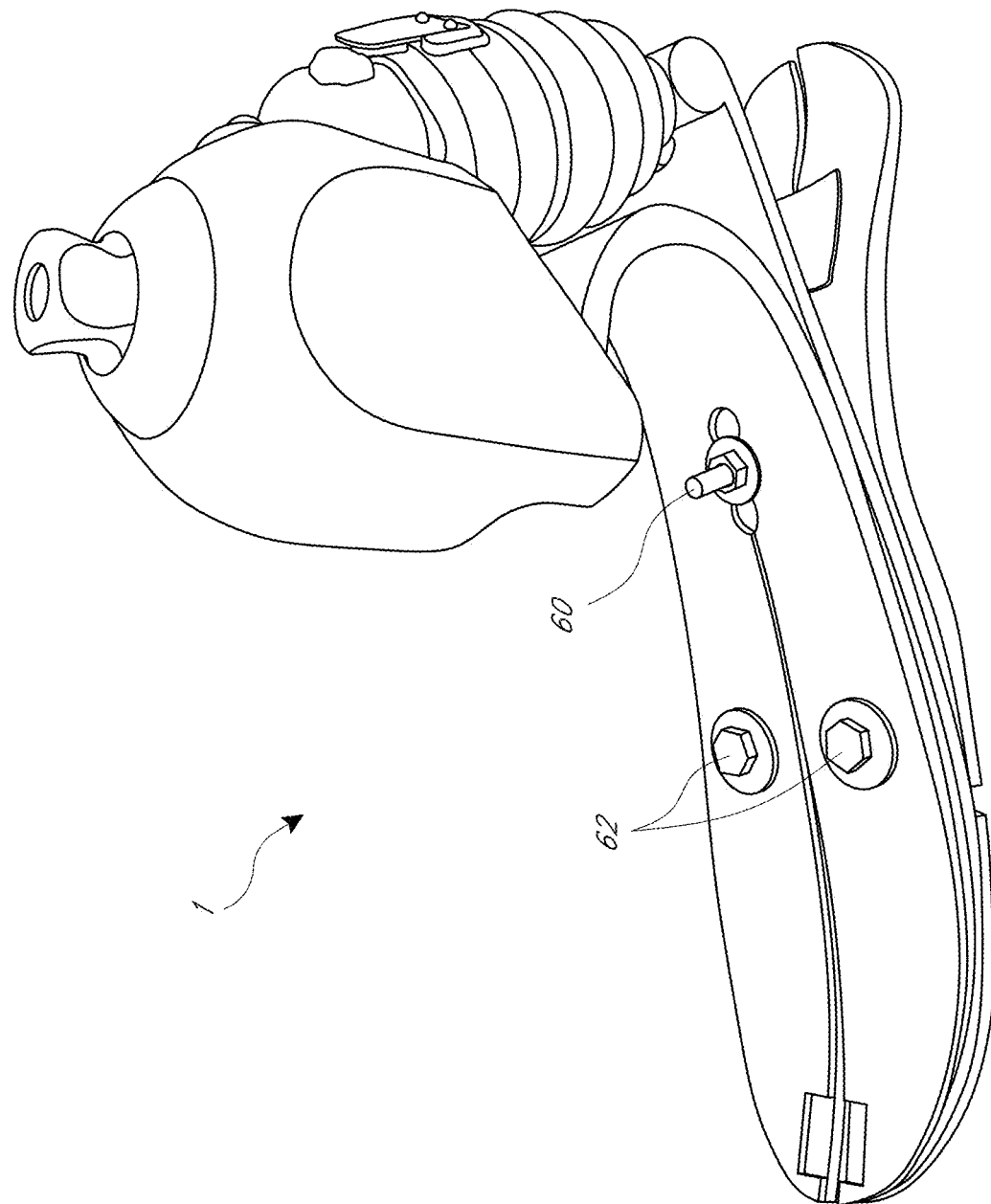
FIG. 8 is a view of the prosthetic foot of FIG. 1 with additional fasteners.
Figure 9:
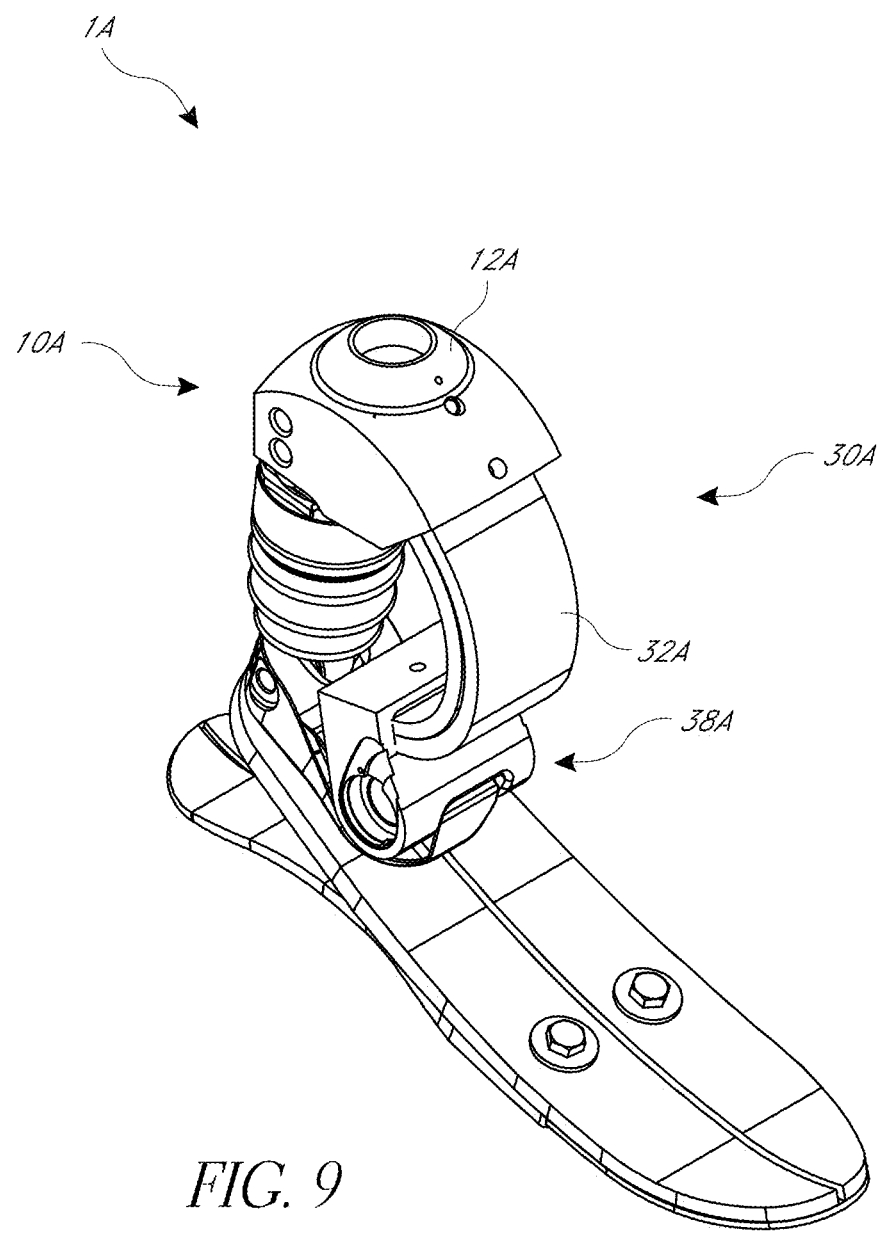
FIG. 9 is a perspective view of another embodiment of a prosthetic foot.
Figure 11:
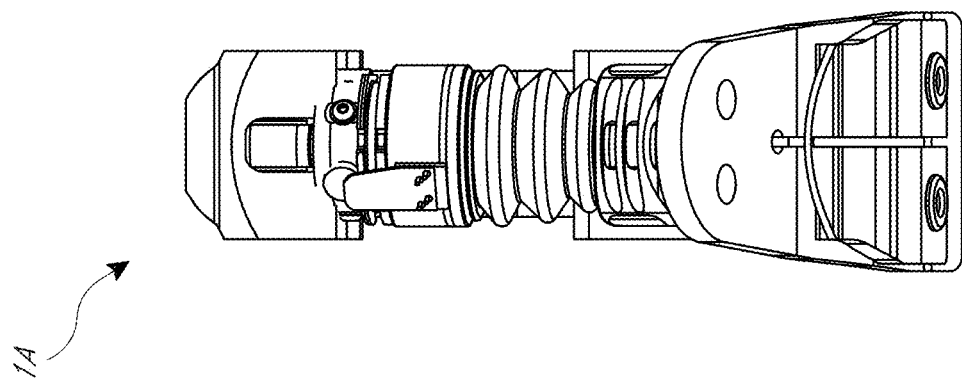
FIG. 11 is a rear view of the prosthetic foot of FIG. 9.
Figure 10:
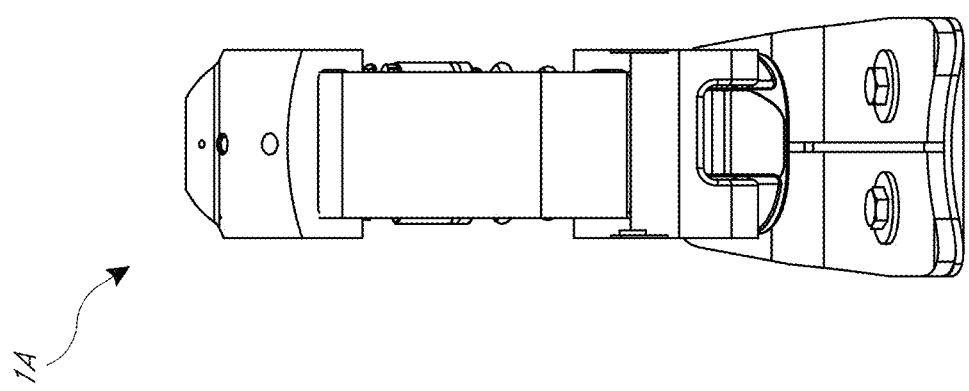
FIG. 10 is a front view of the prosthetic foot of FIG. 9.
Figure 12:
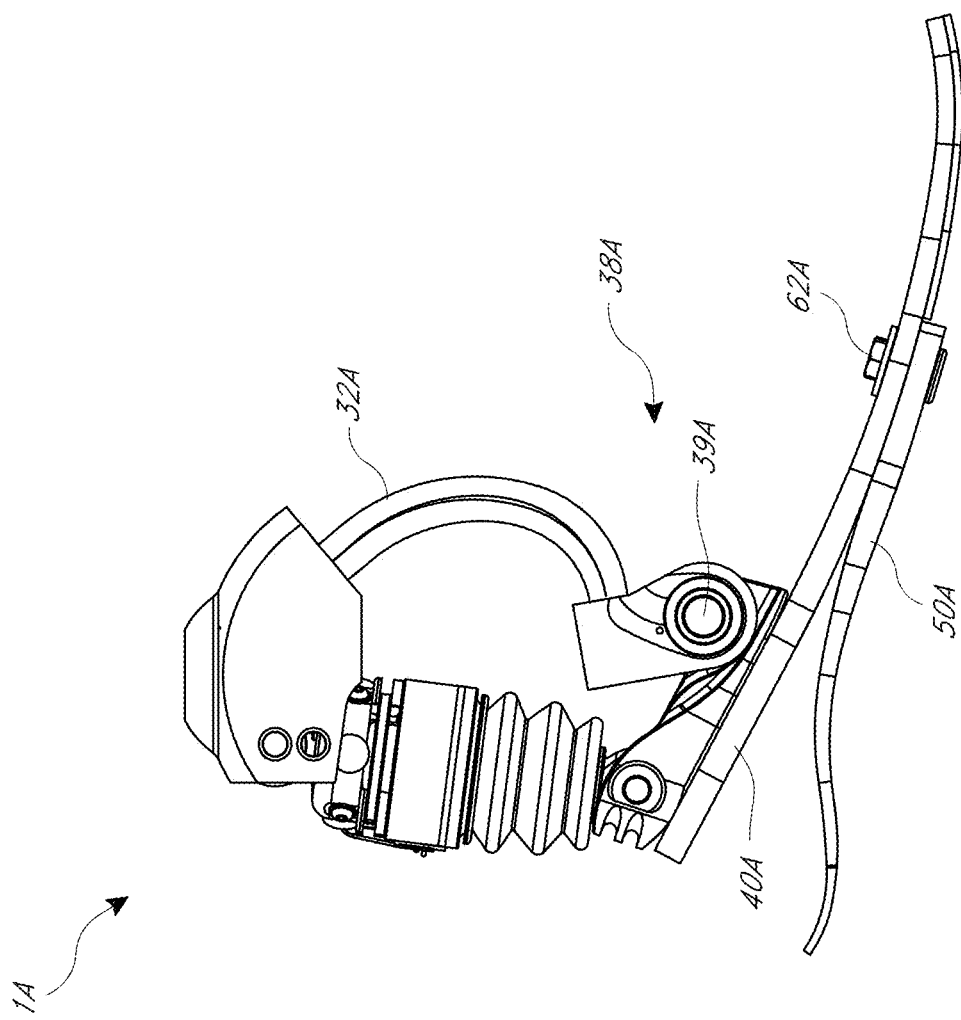
FIG. 12 is a side view of the prosthetic foot of FIG. 9.
Figure 13:
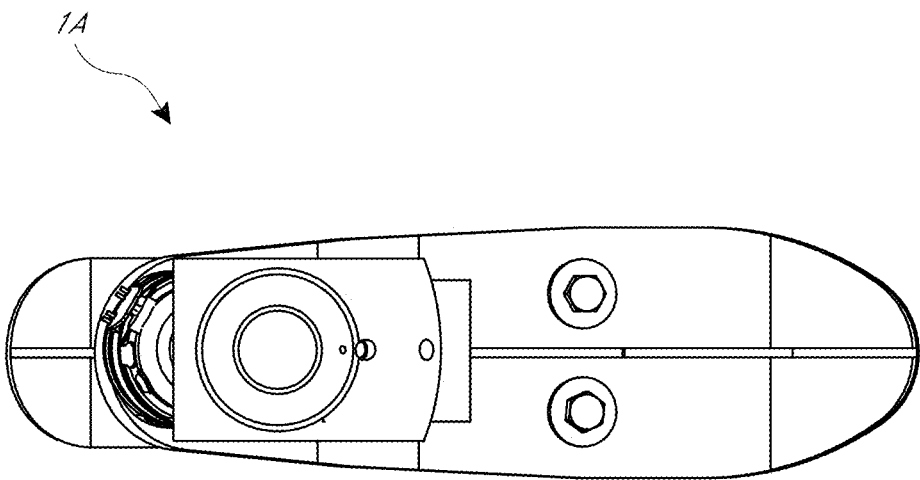
FIG. 13 is a top view of the prosthetic foot of FIG. 9.
Figure 14:
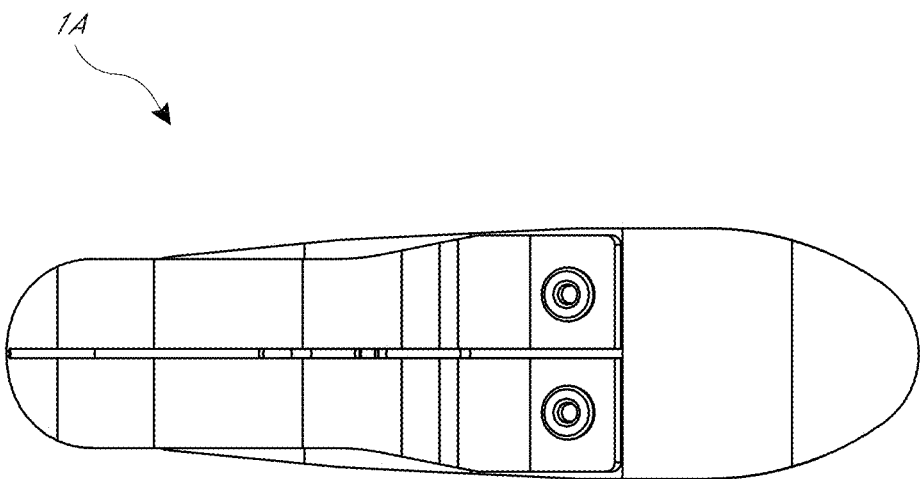
FIG. 14 is a bottom view of the prosthetic foot of FIG. 9.

The actuator 20 is depicted as connecting to a second elastic member 40 at a fourth connection portion 22. Like the second and third connection portions 14, 16, the fourth connection portion 22 can be rotatable or non-rotatable. In one embodiment, the second elastic member 40 can include or define a bushing or opening through which an axle extends to provide a rotatable connection or pivot axis between the second elastic member 40 and the actuator 20. The second elastic member 40 can extend into a foot portion in a manner similar to the foot portion 34 of the first elastic member 30. In one embodiment, the second elastic member 40 can extend to a distal end of the prosthetic foot 1, so that the first and second elastic members 30, 40 extend to generally the same location at the distal end of the prosthetic foot 1. Further, the second elastic member 40 can include a slit similar to the slit 36 of the first elastic member 30. Even further, the second elastic member 40 can be composed of materials similar to those for the first elastic member, such as carbon fiber. As shown, the second elastic member 40 is disposed below the first elastic member 30, and extends tangentially forward and toward the first elastic member to abut the first elastic member 30 along the foot portion 34 of the first elastic member 30. Although the first and second elastic members 30, 40 are depicted as ending at approximately the same point at a toe portion of the prosthetic foot, in some embodiments the first elastic member 30 may extend further, or the second elastic member 40 may extend further. For example, as depicted in FIG. 4A, the first and third elastic members 30, 50 can extend further than the second elastic member 40, creating a gap between the first and third elastic members 30, 50. In other embodiments, a gap can be provided between the first and second elastic members 30, 40 in a toe region of the prosthetic foot, as shown in FIG. 8. As a further example, as depicted in, for example, FIG. 12 the third elastic member 50 (e.g., member 50A, described below) can end before a toe portion of the prosthetic foot 1, such as at a metatarsal region of the foot. The first and/or second elastic members 30, 40 (e.g., only second elastic member 40A in FIG. 12) can then extend past the third elastic member 50 to the toe portion.

The prosthetic foot 1 can further include a third elastic member 50. As shown, the third elastic member 50 can extend from a heel portion 56 (e.g., a cantilevered or free end) at a bottom and rear portion of the prosthetic foot 1. This heel portion 56, as shown, can be spaced from the actuator 20 and the second elastic member 40, curving downward toward and away from the actuator 20. From the heel portion 56, the third elastic member 50 can extend to a toe portion of the prosthetic foot 1, and can generally abut the foot portion second elastic member 40, as that member abuts the first elastic member 30. Further, the third elastic member 50 can have a slit along this foot portion that generally matches the slits in the first and second elastic members 30, 40. Additionally, as shown, the third elastic member 50 can include a heel slit 54 in the heel portion 56 of the elastic member.

As shown in the figures, the slit 36 in the first elastic member 30 can align with the slit in the second elastic member 40 and the slit 52 in the third elastic member 50 in the foot portion 34. In one embodiment, the prosthetic foot 1 can have a stiffness control member 60 that can be actuated to vary the stiffness of the prosthetic foot. In some embodiments, the stiffness control member 60 can be a fastening member 60 (e.g., bolt and nut, clamp, staple, rivet, etc.) that couples two or more of the elastic members 30, 40, 50 to each other, where the fastening member 60 can travel along the slit 36 or a slot defined at least partially by the slit, best shown in FIG. 8, or travel along a slot in the elastic members 30, 40, 50 where the elastic members do not have a slit. Attachment can be provided between the elastic elements 30, 40, 50, for example, generally in a metatarsal region of the prosthetic foot 1. Advantageously, in some embodiments the fastening member's 60 position can be adjustable along the length of the slit 36. For example, when the fastening member 60 is a bolt and nut, the bolt can be moved to any desired position along the slit 36 and then fastened into place by tightening the nut. In some embodiments, an undercut or recess in the elastic members 30, 40, 50 can be provided to prevent the bolt and nut from protruding outwards. Notably, the position of the fastening member along the slit 36 can alter the flexibility and resistance of the elastic members 30, 40, 50. Where the elastic members 30, 40, 50 are not held together (e.g., by the fastening member) they can separate and act as distinct elastic members instead of combining into a single elastic member where held together. Thus, if the fastening member 60 is moved forward, the elastic members 30, 40, 50 are held together over a shorter range, allowing more separation between them, and thus greater flexibility (e.g., the lever arm of the second elastic member 40 is relatively longer, resulting in greater flexibility of the prosthetic foot 1). Alternatively, if the fastening member is moved rearward, the elastic members 30, 40, 50 are held together over a longer range, reducing the allowed separation and flexibility (e.g., the lever arm of the second elastic member 40 is relatively shorter, resulting in increased stiffness of the prosthetic foot 1). Advantageously, the fastening member 60 can be adjusted to vary the stiffness of the prosthetic foot 1.

In some embodiments, the stiffness control member 60 can be mechanically actuated, either manually by the user or automatically (e.g., actively adjusted) during ambulation by the user (e.g., based on the activity level of the user or the phase of gait cycle).

Notably, as discussed above, in some embodiments, the flexibility and resistance of the elastic members 30, 40, 50 can also be altered by the actuator 20 (independently of, or in combination with, the stiffness control member 60). Thus, it will be understood that the flexibility and resistance of the elastic members 30, 40, 50 can be altered manually and/or by an actuator. In further examples, the stiffness control member 60 can be moved (e.g., automatically moved) by an actuator to adjust the resistance and flexibility of the elastic members 30, 40, 50.

In some embodiments, it may be preferable to adjust the flexibility and resistance of the elastic members 30, 40, 50 to reduce resistance and increase flexibility while moving on level ground. Thus, for example, the stiffness control member 60 can be moved forward while ambulating on level ground to provide faster plantarflexion after heel strike. During other gait patterns, such as walking downstairs, one can reduce flexibility and increase resistance by moving the stiffness control member 60 backward. In some embodiments, these gait patterns can be detected by sensors and processors provided on or in communication with the prosthetic foot 1. An actuator can then be controlled to adjust the flexibility and resistance of the elastic members 30, 40, 50 according to the detected gait pattern.

Variations to the embodiment in FIGS. 1-8 are possible. For example, in the depicted embodiment a stiffness control member 60 (e.g., fastening member 60) can be moved to various positions along the slit 36, such that the resistance and flexibility of the elastic members 30, 40, 50 can be varied. However, in other embodiments it may be preferable to remove the slit 36 such that the elastic members 30, 40, 50 are more solid and provide a more uniform resistance. Further, in some embodiments it may be preferable to bond the elastic elements 30, 40, 50 in another manner, such as with an adhesive, so they remain permanently attached. The elastic elements 30, 40, 50 can also be held together with additional fastening members 62, depicted as nuts and bolts in FIG. 8, in addition to the adjustable fastening member 60. In other embodiments, one or more of the elastic elements 30, 40, 50 can be formed together into a single piece. For example, in some embodiments the second and third elastic members 40, 50 can be formed as a single piece.

In further embodiments this resistance can be varied by other methods. For example, in some embodiments the stiffness control member can be a wedge or insert that can be inserted where two or more of the elastic members 30, 40, 50 meet. For example, a wedge can be inserted between the first and second elastic members 30, 40 (e.g., above the second and below the first). Similarly, a wedge can be inserted between the second and third elastic members 40, 50, such as at a wedging location 64, depicted in FIG. 4. The wedge can limit the range of motion of the elastic members 30, 40, 50 relative to each other, thus increasing their resistance. The size and shape of the wedge can be chosen to cause a particular desired resistance. Further, the wedge can be moved forward or rearward to vary the flexibility and resistance between the elastic members 30, 40, 50.

The depicted embodiment also combines three separate elastic elements 30, 40, 50 that each provide a separate function. For example, the first elastic element 30 acts as a spring in parallel with the actuator 20. Further, the second elastic element 40 acts as a spring in series with the actuator 20. Both elastic elements 30, 40 can thus be configured to work with or against the actuator 20 at different phases of the gait cycle. Further, the elastic elements 30, 40 can be loaded or unloaded by the actuator 20. Providing one spring in parallel and the other in series allows each spring to have a different effect on the dynamics of the prosthetic foot 1 during movement. For example, during heel strike, the actuator 20 and second elastic member 40 can act in series to provide the prosthetic foot 1 with a certain level of flexibility in addition to the energy stored by the third elastic member (e.g., be relatively less stiff at heel-strike), while during toe-off, the actuator 20 and first elastic element 30 can act in parallel to provide the prosthetic foot with a different level of flexibility (e.g., be relatively more stiff at toe-off). Thus, the independent flexibility and resistance of the elastic elements 30, 40 can be chosen separately to optimize the behavior of the prosthetic foot 1.

Notably, in the depicted embodiment the first and second elastic members 30, 40 both extend toward the toe along the foot portion 34. However, they do not extend toward the heel of the prosthetic foot 1. The third elastic member 50 includes a heel portion 56. The heel portion 56 thus provides flexibility and resistance to the prosthetic foot 1 during heel strike. This response during heel strike can be determined independently of a flexibility and resistance during toe-strike or toe-off during a gait cycle, as the third elastic element 50 is a separate piece from the first and second elastic elements 30, 40. Thus, for example, a system of separate elastic members 30, 40, 50 can include versions of each elastic member with varying flexibilities and resistances. One can then choose each elastic member 30, 40, 50 to provide a desired flexibility and resistance at different times during a gait cycle, depending on the needs of a particular user.

In further embodiments, the actuator 20 can be removed or replaced with a rigid member. For example, in some embodiments the second elastic member 40 can connect directly to the second connection portion 14. In such embodiments, the first and second elastic members 30, 40 can both be rotatably connected to the attachment member 10. Further, in embodiments where the second elastic member 40 does not connect directly to the second connection portion 14, it can still rotatably connect to an intermediary member (such as a rigid member replacing the actuator 20) at a fourth connection portion 22 (as described above). In such embodiments, the three rotatable connections 14, 16, 22 can form a triangle with at least one elastic portion, the elastic portion being both the first and second elastic members 30, 40, between the fourth connection portion 22 and the third connection portion 16.

The rotatable connections 14, 16, 22 with the elastic members 30, 40 can provide a flexible resistance to rotation of the attachment member 10. Advantageously, the use of both first and second elastic members 30, 40 can provide for a natural rocking motion during stance that can provide improved stability with the prosthetic foot 1. This stability can also be provided in embodiments that include an actuator 20, e.g., when the actuator 20 is locked in a particular position or is substantially inactive.

FIGS. 9-15 depict a second embodiment of a prosthetic foot 1A. It will be understood that the prosthetic foot 1A in these figures has features similar to the prosthetic foot 1 described above, and thus will be described in terms of its differences. As shown, the prosthetic foot 1A includes a first elastic member 30A having a C-shaped portion 32A, similar to that in the previously described embodiments. However, in the present embodiment the C-shape portion 32A can be reversed to have an opening facing rearward (e.g., the C-shaped portion 32A has a concave shape facing toward the rear of the prosthetic foot 1). Further, as shown, the first elastic member 30A can include two parallel elastic pieces. Additionally, as shown, the first elastic member 30A can attach to the attachment member 10A at a second connection portion 14A that is non-rotatable, although in other embodiments the second connection portion 14A can be rotatable (e.g., via a pivot location, as shown in previous embodiments). Further, as shown, the first elastic member 30A can be shortened to not include a foot portion, like the foot portion 34 in the previous embodiments. Instead, the first elastic member 30A can attach to a fifth connection body 38A, also via a non-rotatable connection. However, the fifth connection body 38A can provide a rotatable connection to the second elastic member 40A, as shown in the figures, via a supplemental connection body 39A that can be considered to be part of the fifth connection body 38A.

Figure 15:
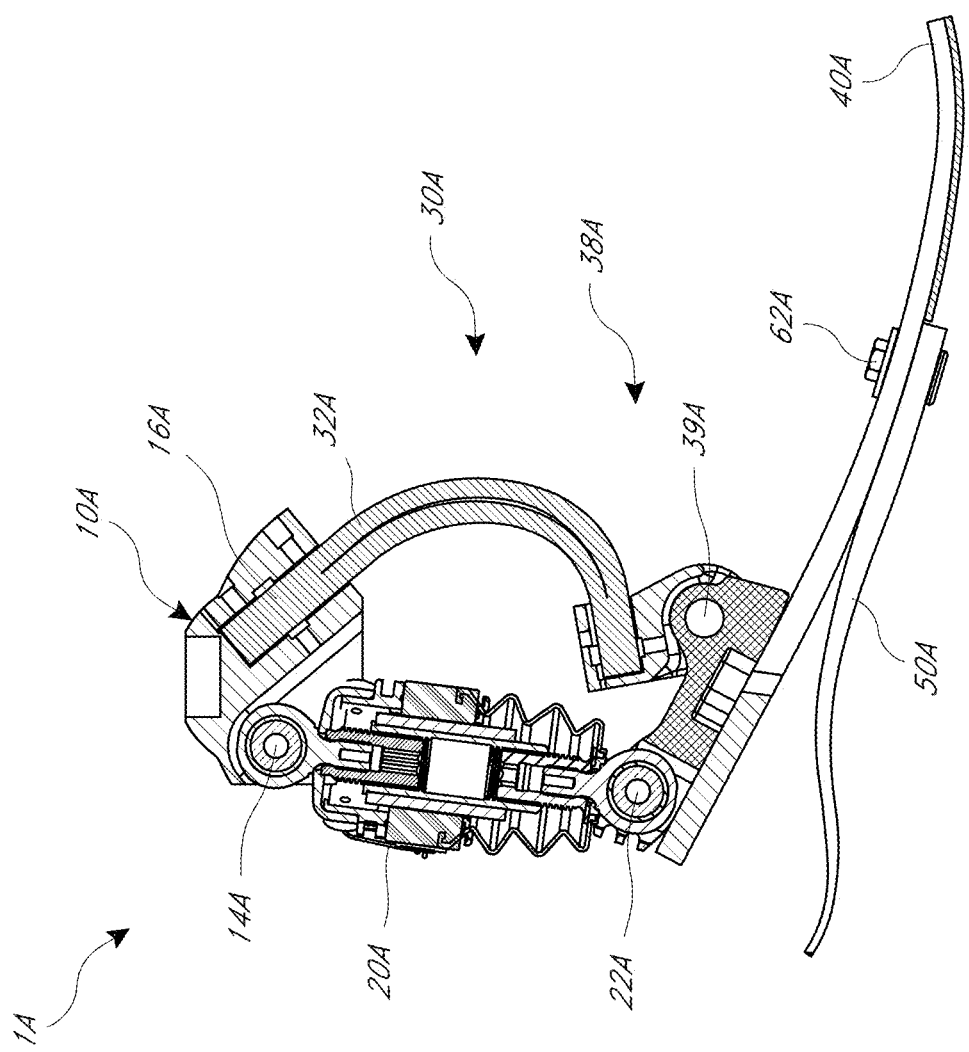
FIG. 15 is a cross-sectional side view of the prosthetic foot of FIG. 9.

Notably, the features in the embodiment in FIGS. 9-15 also form a triangle with at least one elastic portion and three rotatable connections, similar to that discussed above in the previous embodiment. For example, as best shown in FIG. 15, the prosthetic foot 1A includes a second connection portion 14A between the attachment member 10A and the actuator 20A. The actuator 20A can include a fourth connection portion 22A, connecting to the second elastic member 40A. The second elastic member 40A can connect to the first elastic member 30A with fifth connection body 59A. The first elastic member 30A can attach to the attachment member 10A, completing the triangle. In some embodiments, only one portion of the triangle can have an elastic portion. For example, in some embodiments the second elastic member 40A can be an inelastic or rigid member.

Figure 15A:
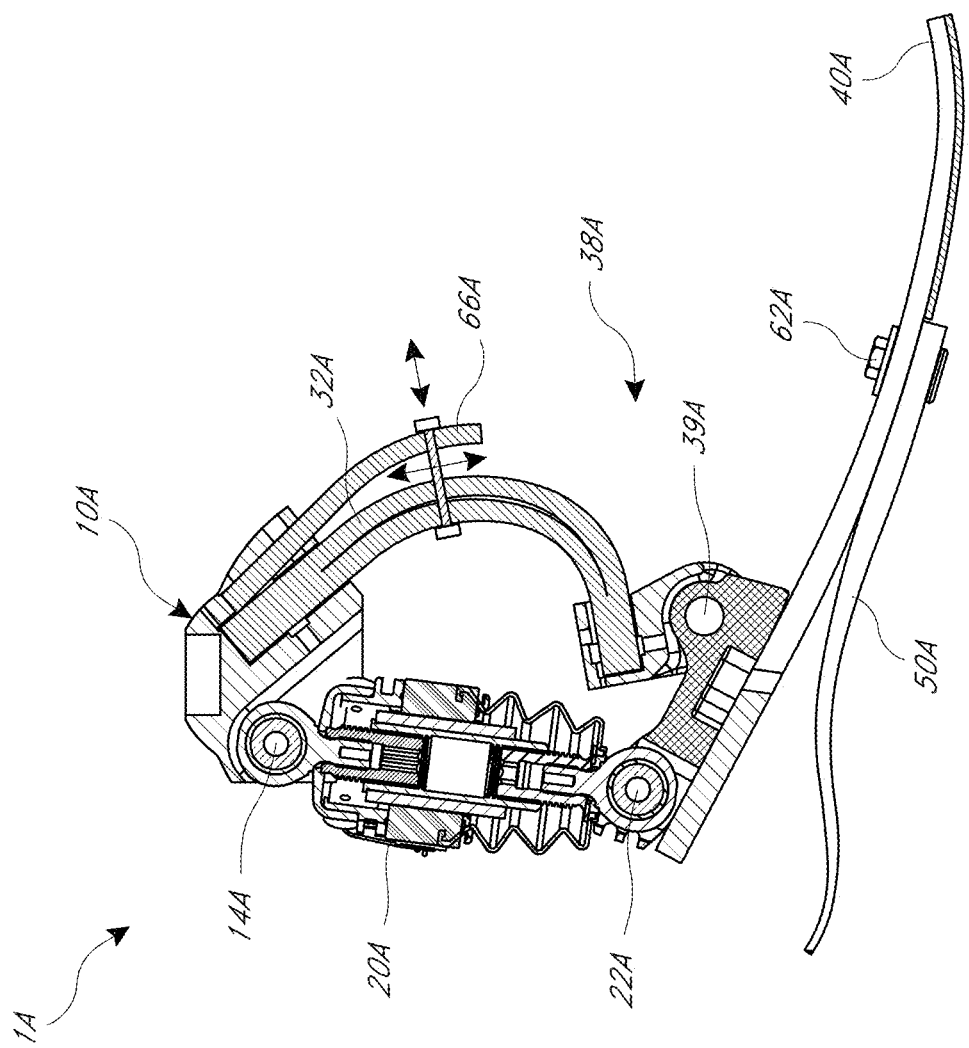
FIG. 15A is a cross-sectional view of another embodiment of a prosthetic foot, similar to the prosthetic foot of FIG. 9.
Figure 16:
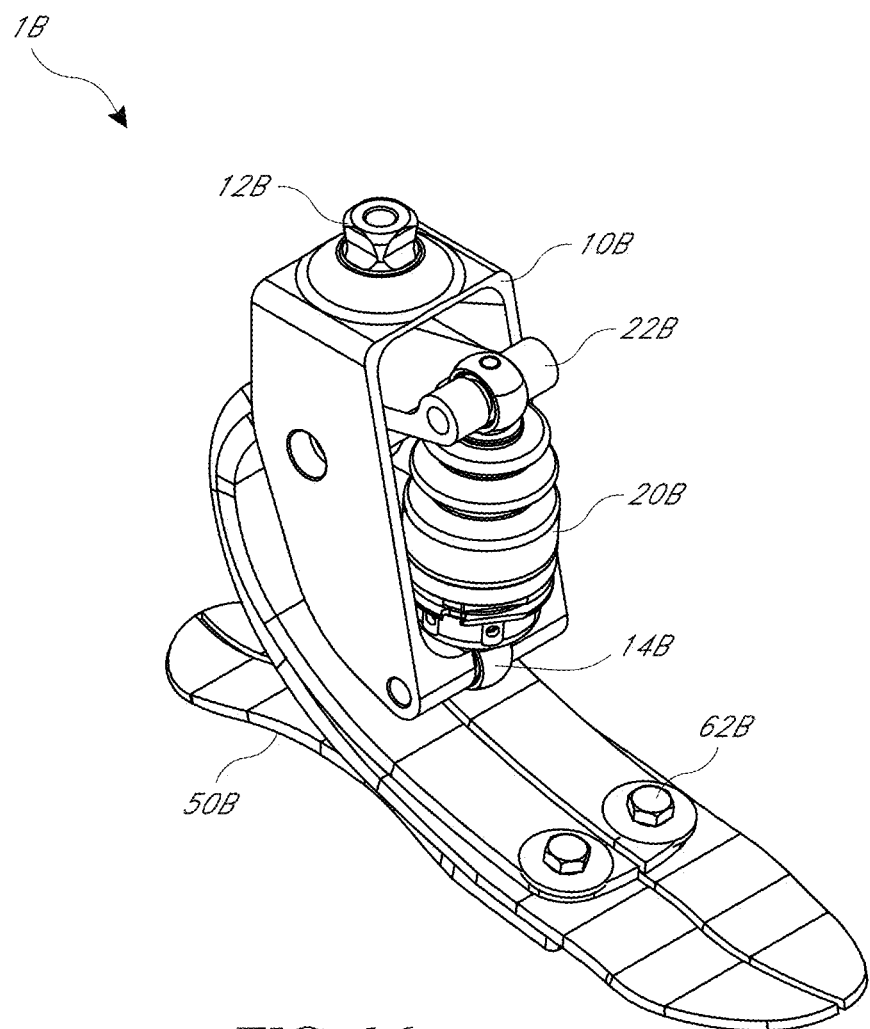
FIG. 16 is a perspective view of another embodiment of a prosthetic foot.
Figure 17:
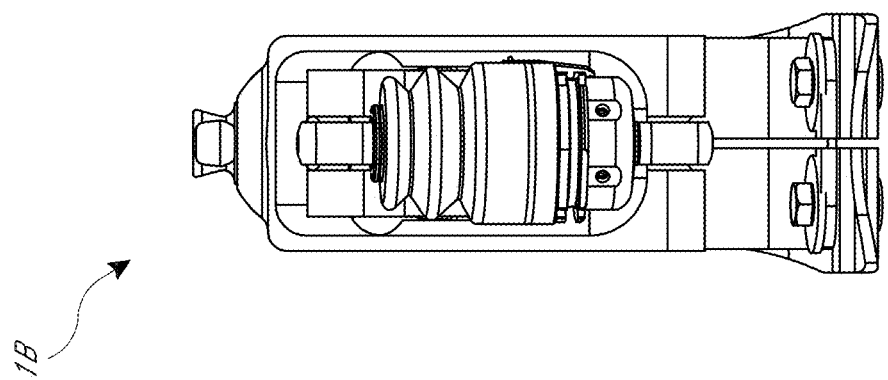
FIG. 17 is a front view of the prosthetic foot of FIG. 16.
Figure 18:
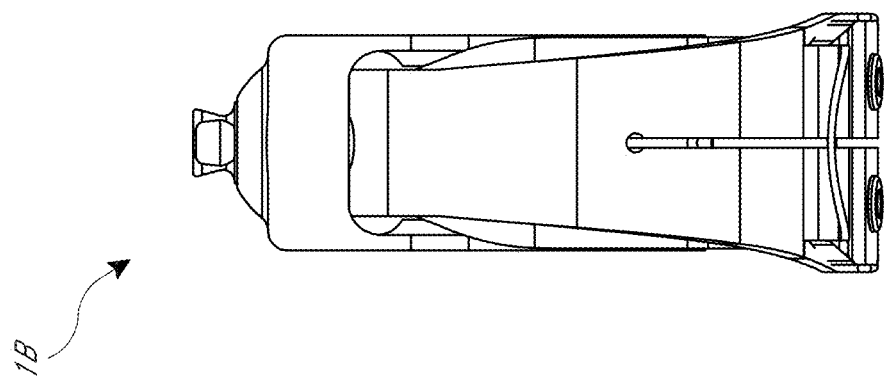
FIG. 18 is a rear view of the prosthetic foot of FIG. 16.
Figure 19:
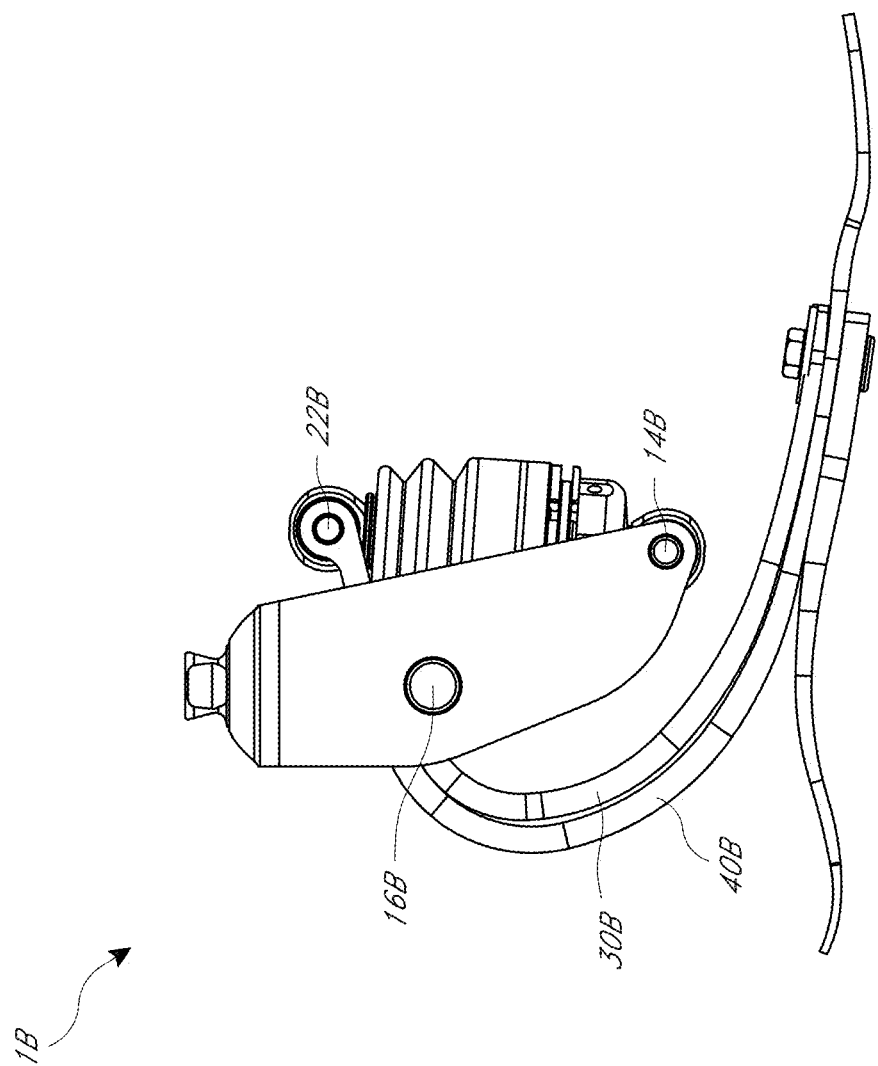
FIG. 19 is a side view of the prosthetic foot of FIG. 16.
Figure 20:
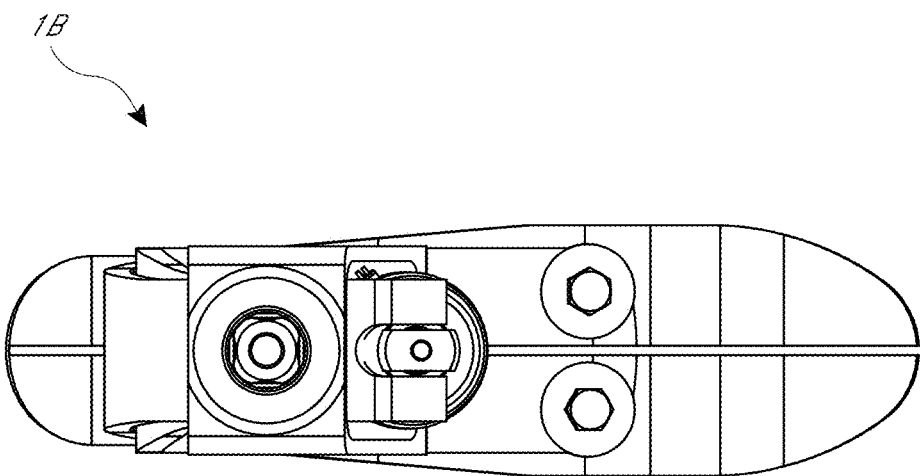
FIG. 20 is a top view of the prosthetic foot of FIG. 16.
Figure 21:
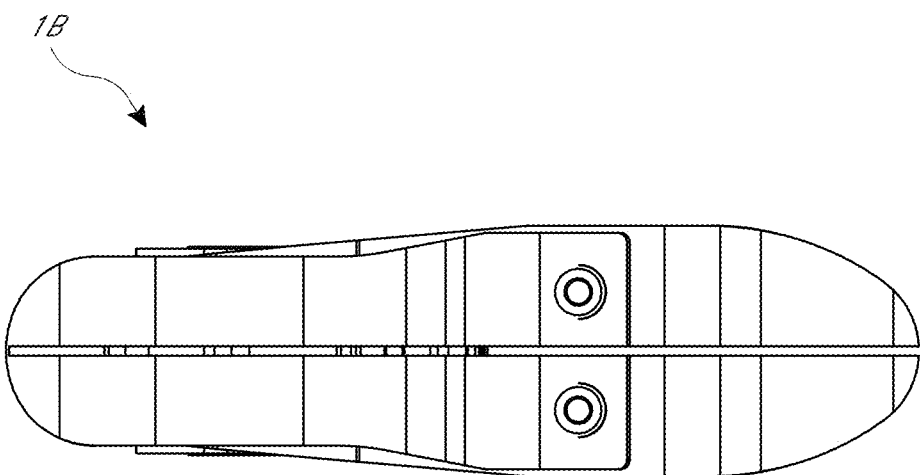
FIG. 21 is a bottom view of the prosthetic foot of FIG. 16.

Further, in some embodiments the C-shaped portion 32A can be substantially similar to that shown in FIGS. 9-15, but include an additional elastic member 66A generally aligned with the C-shaped portion 32A, as best shown in FIG. 15A. The additional elastic member 66A can connect to the attachment member 10A in a manner similar to the first elastic member 30A. The additional elastic member 66A can then extend tangent with the first elastic member 30A along the C-shaped portion 32A and terminate at a free end unattached to the fifth connection body 39A. A stiffness control member similar to the stiffness control member 60 can then be provided between the C-shaped portion 32A and the additional elastic member 66A. For example, slits can be provided in the C-shaped portion 32A and the additional elastic member 66A to receive a fastening member that can be moved along the length of the slit to adjust the flexibility and resistance of the C-shaped portion 32A, as illustrated. In further embodiments, such adjustability of the flexibility and resistance of the elastic members 30A, 40A, 50A can be provided with other suitable mechanisms. For example, in some embodiments the fifth connection body 38A (including the supplemental connection body 39A) can be movable in an anterior-posterior direction along the second elastic member 40A to change the location of the fifth connection body 38A on the second elastic member 40A. For example, in some embodiments the second elastic member 40A can include a slot that can receive a fastener to fasten the fifth connection body 38A in place along the second elastic member. However, other suitable mechanisms can be used to adjust the location of the fifth connection body 38A relative to the second elastic member 40A (e.g., a track and worm gear arrangement).

Additionally, the depicted prosthetic foot 1A depicts an alternative method for attaching the second and third elastic members 40A, 50A. As shown, these members can be attached by two bolts 62A, on opposite sides of the slit 36A. However, it will be understood that other attachment methods can be used, such as those described above. Further, an adjustable fastening member can be provided in the slit 36A, as discussed above, to vary the flexibility and resistance of the prosthetic foot 1A.

FIGS. 16-23 depict yet another embodiment of a prosthetic foot 1B. It will again be understood that the prosthetic foot 1B in these figures has features similar to the prosthetic foot 1 described above, and thus will be described in terms of its differences. As shown, the prosthetic foot 1B provides a design with the actuator 20B in a forward portion of the prosthetic foot. As shown, the attachment member 10B can still attach to the first elastic element 30B at a rotatable third connection portion 16B. However, the third connection portion 16B can be provided at an upper rear portion of the attachment member 10B. The second connection portion 14B can connect to the actuator 20B at a lower forward portion of the attachment portion 10B. The actuator 20B can then extend upwards from the second connection portion 14B to attach to the second elastic member 40B. The second elastic member 40B can then form a C-shaped portion that follows the forward-facing C-shaped portion 32B in the first elastic member 30B.

Connection of the third elastic member 50B is depicted as being substantially similar to the third elastic member 50A depicted in FIGS. 9-15. Similar variations can also be provided, as discussed above. Further, as shown, the first elastic member 30B can extend to a foot portion 34A and attach to the second and third elastic members 40B, 50B by the same bolts 62B. Further, as shown, the second elastic member 40B can extend beyond the first and second elastic members 30B, 50B, to a toe portion of the prosthetic foot 1B.

Figure 22:
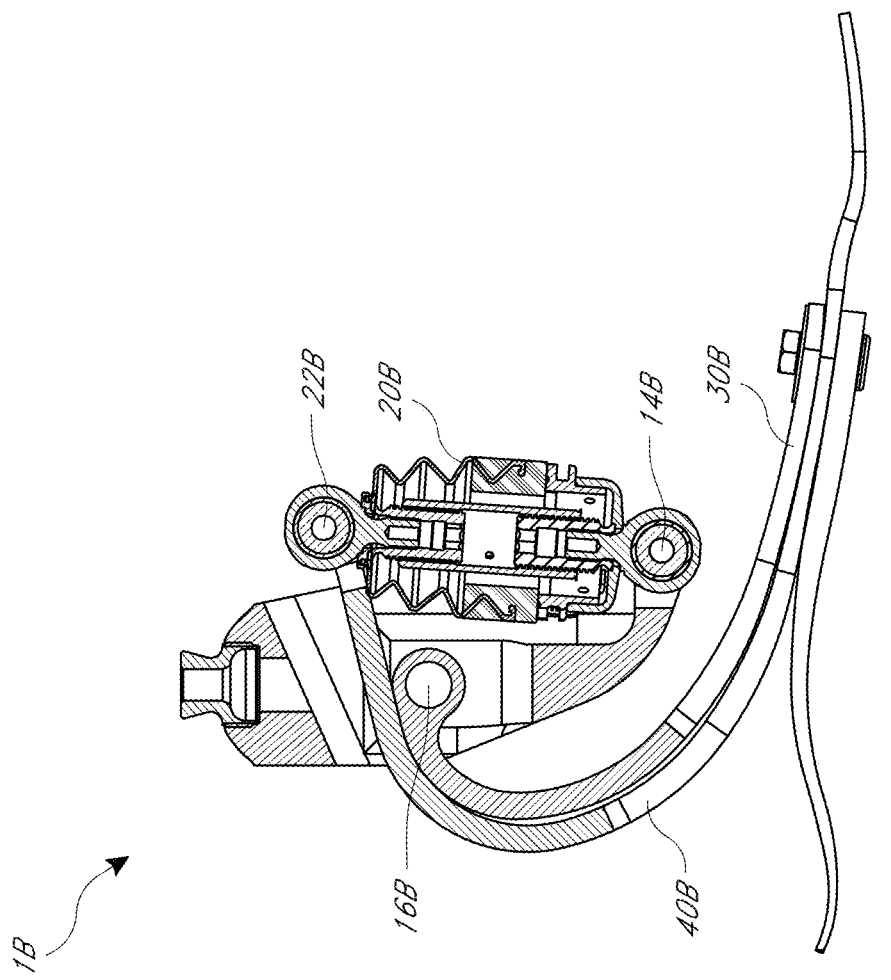
FIG. 22 is a cross-sectional side view of the prosthetic foot of FIG. 16.

Notably, the features in the embodiment in FIGS. 16-23 also form a triangle with at least one elastic portion and three rotatable connections, similar to that discussed above in the previous embodiments. For example, as best shown in FIG. 22, the prosthetic foot 1B includes a second connection portion 14B between the attachment member 10B and the actuator 20B. The actuator 20B can include a fourth connection portion 22B, connecting to the second elastic member 40B. The second elastic member 40A can come to abut the first elastic member 30B, as described above regarding the previous embodiments. The first elastic member 30B can attach to the attachment member 10B at the third connection portion 16B, completing the triangle.

Figure 23:
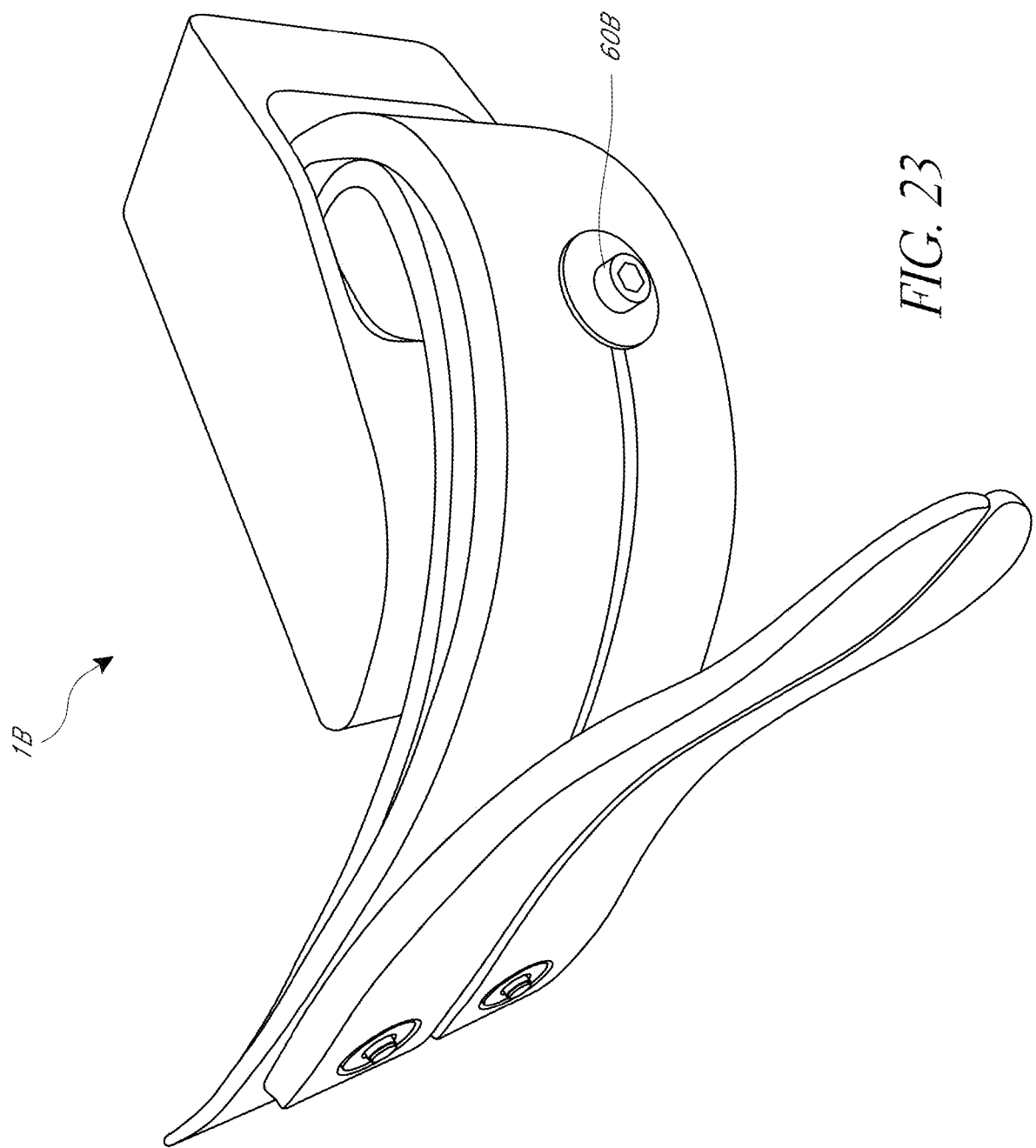
FIG. 23 is a view of the prosthetic foot of FIG. 16 with an additional fastener.

Further, as best shown in FIG. 23, the first and second elastic members 30B, 40B can be connected by a stiffness control member 60B. In the illustrated embodiment, the stiffness control member 60B is an adjustable fastening member 60B and can allow for varied resistance and flexibility in a manner similar to that in the embodiments discussed above. In the present embodiment, the adjustable fastening member 60B is provided between only the first and second elastic members 30B, 40B (and not the third elastic member 50B), and in a rear portion of the prosthetic foot 1B. Moving the adjustable fastening member 60B downward and forward results in a lever arm of the first and second elastic members 30B, 40B between the fastening member 60B and the attachment member 10B that is relatively longer, resulting in increased flexibility of the prosthetic foot 1B. Alternatively, moving the adjustable fastening member 60B upward results in a lever arm of the first and second elastic members 30B, 40B between the fastening member 60B and the attachment member 10B that is relatively shorter, resulting in increased stiffness of the prosthetic foot 1B.

Advantageously, the prosthetic foot 1, 1A, 1B embodiments disclosed can provide for a natural rocking motion during a stance phase of gait that can provide improved stability to the prosthetic foot 1, 1A, 1B (e.g., the attachment member 10, 10A, 10B can move relative to one or more of the elastic members during stance). This improved stability can also be provided in embodiments that include an actuator 20, 20A, 20B, e.g., when the actuator 20, 20A, 20B is locked in a particular position or is substantially inactive. Additionally, in some embodiments, the prosthetic foot can include a stiffness control member that can be mechanically actuated (e.g., manually or automatically) to vary a stiffness of one or more elastic members of the prosthetic foot to provided different levels of stiffness (e.g., during different types of gait).

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others. Additionally, features described in connection with one embodiment can be incorporated into another of the disclosed embodiments, even if not expressly discussed herein, and the prosthetic device having the combination of features still fall within the scope of the invention.

What is claimed is:

1. A prosthetic foot with improved stability, the prosthetic foot comprising:

an attachment member disposed at an ankle position of the prosthetic foot, the attachment member comprising a first connection portion configured to connect the attachment member to a user or another prosthetic device, the first connection portion including a pyramid connector;

a rigid member coupled to a posterior portion of the attachment member by a second connection portion at a first end of the rigid member, the second connection portion being a rotatable connection, the first end of the rigid member being closer to the attachment member;

a first elongate member coupled to an anterior portion of the attachment member by a third connection portion and extending forward toward a toe portion of the prosthetic foot, the third connection portion being a rotatable connection;

a second elongate member coupled to a second end of the rigid member by a fourth connection portion at a heel end of the second elongate member, the second end of the rigid member being opposite the first end of the rigid member and closer to a heel end of the prosthetic foot than the first end of the rigid member; and a third elongate member disposed below the first elongate member and the second elongate member to contact a ground surface while the prosthetic foot is in use, the third elongate member extending from a toe end to the heel end of the prosthetic foot, wherein the third elongate member is disposed below the second elongate member along an entire length of the third elongate member, and wherein rotation of the first and second elongate members relative to the attachment member can be caused by contact between the prosthetic foot and the ground surface, independent of other forces, to provide a rocking motion during a stance phase of gait.

2. The prosthetic foot of claim 1, wherein the attachment member comprising a housing cover.

3. The prosthetic foot of claim 1, wherein the first and second elongate members extend to generally the same location at distal ends of the first and second elongate members.

4. The prosthetic foot of claim 1, wherein the first elongate member is flexible.

5. The prosthetic foot of claim 1, wherein the second elongate member is flexible.

6. The prosthetic foot of claim 5, wherein the second elongate member is disposed below the first elongate member.

7. The prosthetic foot of claim 1, wherein the third elongate member is flexible.

8. The prosthetic foot of claim 7, wherein, during heel strike, the rigid member and the second elongate member are configured to act in series to provide the prosthetic foot with a first level of flexibility in addition to energy stored by the third elongate member.

9. The prosthetic foot of claim 8, wherein, during toe-off, the rigid member and the first elongate member are configured to act in parallel to provide the prosthetic foot with a second level of flexibility different from the first level of flexibility.

10. The prosthetic foot of claim 1, wherein the second, third, and fourth connection portions form a triangle with at least one elastic portion between the fourth connection portion and the third connection portion.

11. The prosthetic foot of claim 10, wherein the elastic portion comprises at least one of the first elongate member or the second elongate member.

12. The prosthetic foot of claim 11, wherein the elastic portion comprises both the first elongate member and the second elongate member.

13. The prosthetic foot of claim 1, wherein the attachment member provides a rigid connection between the first connection portion, the second connection portion, and the third connection portion.

14. The prosthetic foot of claim 1, wherein the attachment member further comprises electronics configured to communicate information to another electronic device.

* * * * *

UNITED STATES PATENT AND TRADEMARK OFFICE
CERTIFICATE OF CORRECTION

| | | |
|---|---|---|
| PATENT NO. | : 12,220,330 B2 | Page 1 of 1 |
| APPLICATION NO. | : 17/677194 | |
| DATED | : February 11, 2025 | |
| INVENTOR(S) | : Arinbjörn Viggo Clausen | |

It is certified that error appears in the above-identified patent and that said Letters Patent is hereby corrected as shown below:

On the Title Page

Page 10, Column 1 Item (56) (Other Publications), Line 27, delete "IEEE IOth International" and insert -- IEEE 10th International --.

In the Specification

Column 6, Line 29, delete "a magnetorheologic fluid," and insert -- a magnetorheological fluid, --.

Column 10, Line 23, delete "a second connection" and insert -- a third connection --.

Column 10, Line 24, delete "portion 14A that" and insert -- portion 16A that --.

Column 10, Line 25, delete "the second connection" and insert -- the third connection --.

Column 10, Line 25, delete "portion 14A can" and insert -- portion 16A can --.

Signed and Sealed this
Twenty-seventh Day of May, 2025

Coke Morgan Stewart
*Acting Director of the United States Patent and Trademark Office*